US012788253B2

(12) United States Patent
Michaeli et al.

(10) Patent No.: US 12,788,253 B2
(45) Date of Patent: Nov. 10, 2026

(54) NON-CONTACT RAPID DIAGNOSIS OF ILLNESS BY LASER, INFRA RED, TERAHERTZ AND/OR UV SPECTROSCOPY AND ANALYSIS OF WATER MIXTURE ENVELOPE

(71) Applicants: David Michaeli, Ashkelon (IL); Menashe Michaeli, Ashkelon (IL); Sviatoslav Tarasenko, Istanbul (TR)

(72) Inventors: David Michaeli, Ashkelon (IL); Menashe Michaeli, Ashkelon (IL); Sviatoslav Tarasenko, Istanbul (TR)

( * ) Notice: Subject to any disclaimer, the term of this patent is extended or adjusted under 35 U.S.C. 154(b) by 0 days.

(21) Appl. No.: 19/017,632

(22) Filed: Jan. 11, 2025

(65) Prior Publication Data

US 2025/0366717 A1 Dec. 4, 2025

Related U.S. Application Data

(63) Continuation-in-part of application No. 18/679,506, filed on May 31, 2024, now abandoned, which is a (Continued)

(51) Int. Cl.
*A61B 5/00* (2006.01)

(52) U.S. Cl.
CPC .......... *A61B 5/0075* (2013.01); *A61B 5/7264* (2013.01)

(58) Field of Classification Search
CPC . A61B 5/0022; A61B 5/0075; A61B 5/14546; A61B 5/01; A61B 5/0816;
(Continued)

(56) References Cited

U.S. PATENT DOCUMENTS 10,517,964 B2 * 12/2019 Gambhir ............ A61K 51/0491
2005/0189216 A1 * 9/2005 Krylov .................. C02F 1/4674
204/263

(Continued)

FOREIGN PATENT DOCUMENTS

KR 20210135867 A 11/2021

OTHER PUBLICATIONS

Huffman, J. et al. 2019. Real-time sensing of bioaerosols: Review and current perspectives. Aerosol Science and Technology, vol. 54, 465-495 (Year: 2019).*

(Continued)

*Primary Examiner* — Anhtuan T Nguyen
*Assistant Examiner* — Dean N Edun
(74) *Attorney, Agent, or Firm* — Shlomo Horowitz; Shlomo Horowitz Patents and Intellectual Property Ltd.

(57) ABSTRACT

A non-contact rapid diagnostic system may include water treated by an electrochemical process, i.e. electrocoagulation, at least one laser and/or infra red device and/or terahertz or UV device configured to direct electromagnetic radiation at a subject and/or an area surrounding the subject containing a water mixture envelope of a sprayed form of the treated water and a low disperse water envelope emitted from the subject's body, spectral imaging programming instructions of a digital processing unit to convert the reflected beam to a spectrogram/image and to store reference spectra of healthy and ill subjects on memory, determine a water fingerprint (i.e. using neural networks) of the water mixture envelope of the subject and determine, based on the water fingerprint and at least one of the stored reference spectra, whether the subject has one or more of a variety of medical conditions and/or what chemical compounds are present, and output the determination.

28 Claims, 13 Drawing Sheets

Related U.S. Application Data continuation-in-part of application No. 18/418,393, filed on Jan. 22, 2024, now abandoned, which is a continuation-in-part of application No. 18/105,855, filed on Feb. 5, 2023, now abandoned.

(58) Field of Classification Search
CPC ... A61B 5/1455; A61B 5/7246; A61B 5/7275; A61B 2010/0087; A61M 16/0808; A61M 16/1065; A61M 16/16
See application file for complete search history.

(56) References Cited

U.S. PATENT DOCUMENTS

| | | | | |
|---|---|---|---|---|
| 2017/0138851 | A1* | 5/2017 | Ashrafi | G01N 33/487 |
| 2020/0253547 | A1 | 8/2020 | Harris et al. | |
| 2021/0369115 | A1 | 12/2021 | Zatvan et al. | |
| 2022/0034854 | A1* | 2/2022 | Chen | A61B 10/00 |
| 2023/0184682 | A1* | 6/2023 | League | A61B 5/746 |
| 2024/0130621 | A1* | 4/2024 | Islam | A61B 5/0088 |
| 2025/0107725 | A1* | 4/2025 | Bierewirtz | G01N 33/497 |

OTHER PUBLICATIONS https://m.nkj.ru/archive/articles/5112 Laser Explores the Atmosphere, O Kostko, (tomsk, Russia 1980).

Jing Xu et al, Biosensors 2021, 11, 245. Wearable Biosensors for Non-Invasive Sweat Diagnostics https://doi.org/10.3390/bios11080245.

* cited by examiner

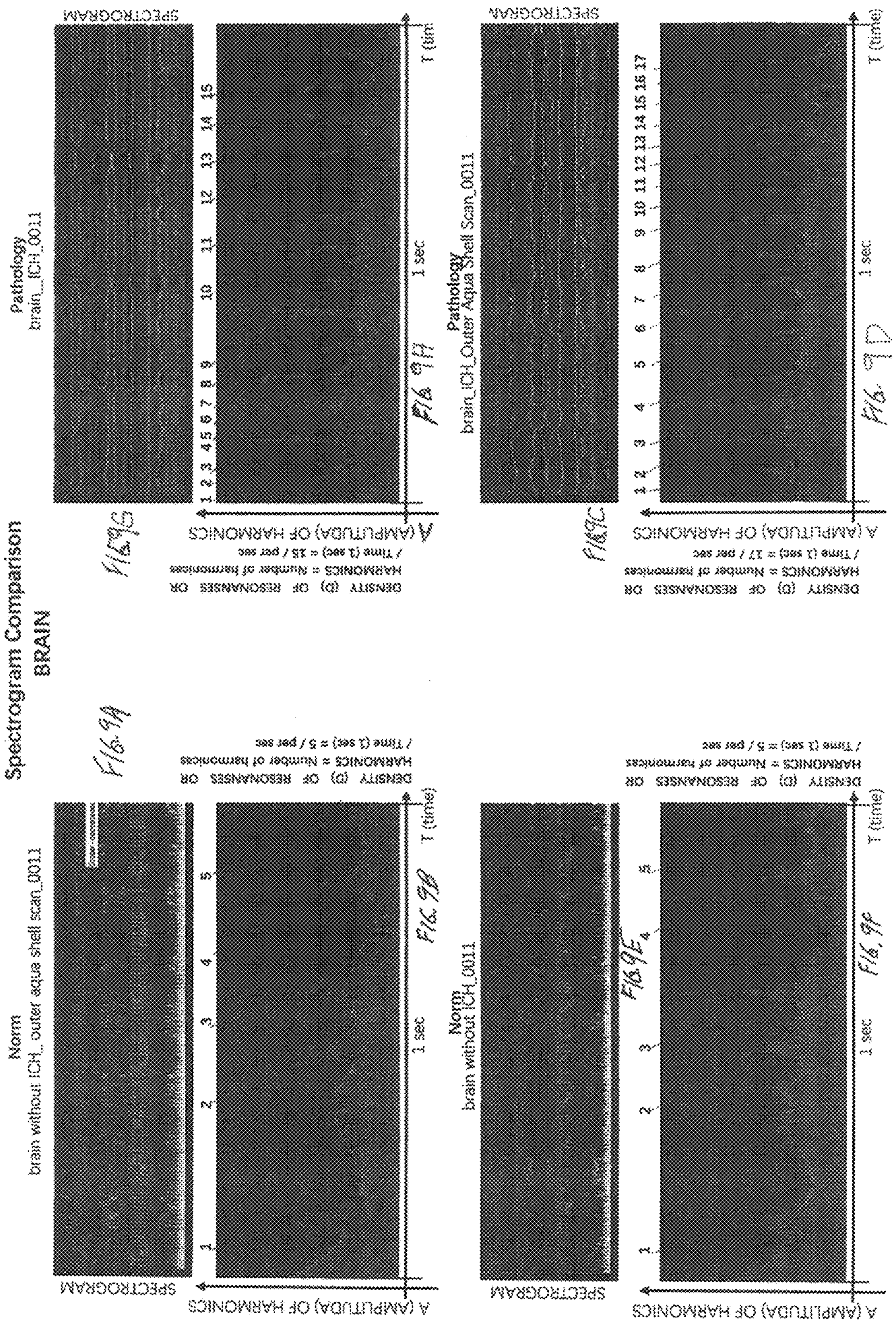
Spectrogram Comparison
BRAIN
Norm
brain without ICH_ outer aqua shell scan_0011
Pathology
brain_ICH_0011
Norm
brain without ICH_0011
Pathology
brain_ICH_Outer Aqua Shell Scan_0011
SPECTROGRAM
A (AMPLITUDA) OF HARMONICS
T (time)
1 sec
DENSITY (D) OF RESONANSES OR HARMONICS = Number of harmonics / Time (1 sec) = 5 / per sec
DENSITY (D) OF RESONANSES OR HARMONICS = Number of harmonics / Time (1 sec) = 15 / per sec
DENSITY (D) OF RESONANSES OR HARMONICS = Number of harmonics / Time (1 sec) = 17 / per sec
FIG. 9A
FIG. 9B
FIG. 9C
FIG. 9D
FIG. 9E
FIG. 9F
FIG. 9G
FIG. 9H 2D Ultrasound with GE Phase Array probe 2.5 MHz CT-Computer Tomography Same Patient

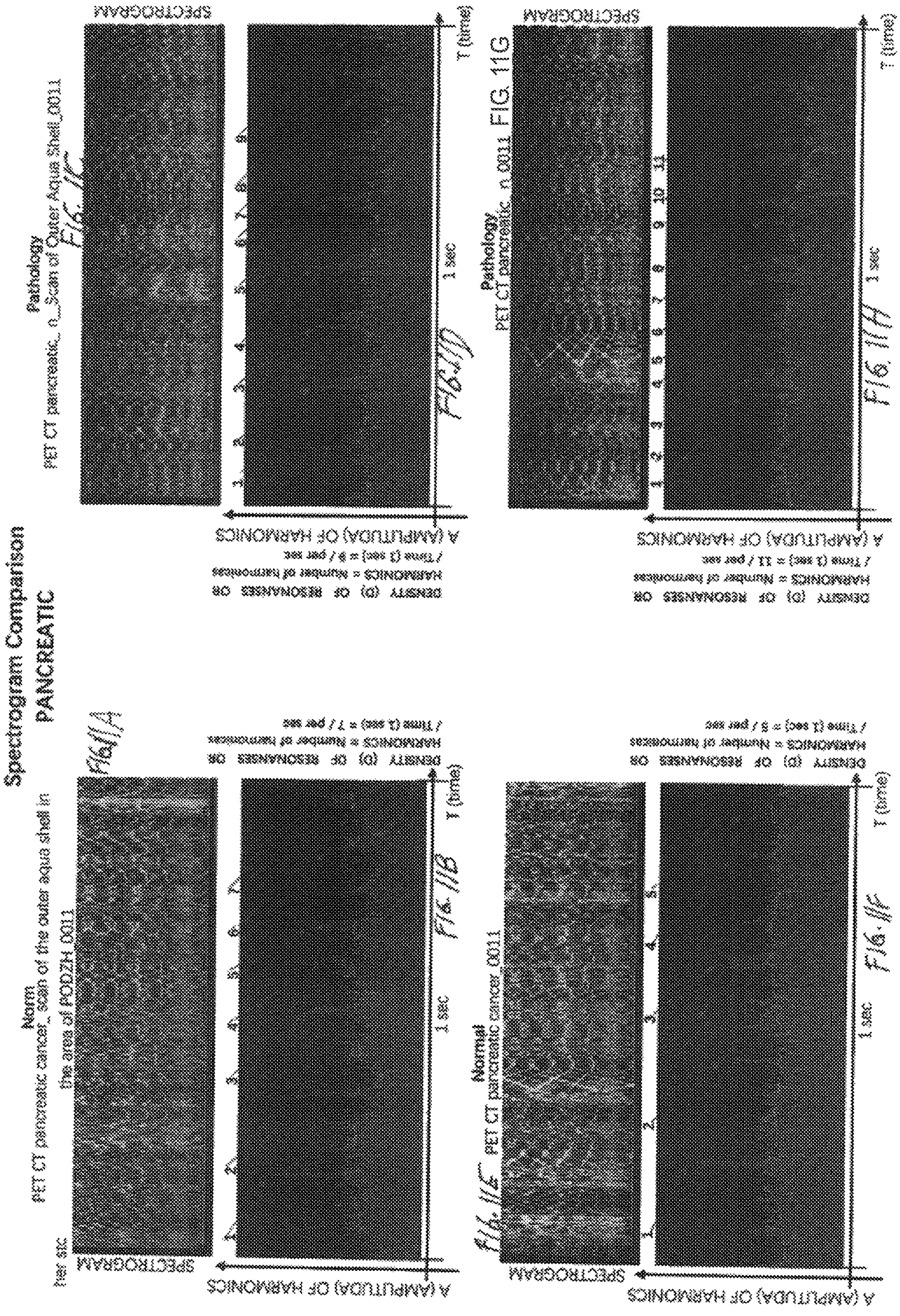
Spectrogram Comparison
PANCREATIC
Norm
PET CT pancreatic cancer_ scan of the outer aqua shell in the area of PODZH 0011
Normal
PET CT pancreatic cancer_0011
Pathology
PET CT pancreatic_ n_Scan of Outer Aqua Shell_0011
Pathology
PET CT pancreatic_ n_0011
SPECTROGRAM
A (AMPLITUDA) OF HARMONICS
T (time)
1 sec
DENSITY (D) OF RESONANSES OR HARMONICS = Number of harmonices / Time (1 sec) = 7 / per sec
DENSITY (D) OF RESONANSES OR HARMONICS = Number of harmonices / Time (1 sec) = 5 / per sec
DENSITY (D) OF RESONANSES OR HARMONICS = Number of harmonices / Time (1 sec) = 9 / per sec
DENSITY (D) OF RESONANSES OR HARMONICS = Number of harmonices / Time (1 sec) = 11 / per sec
FIG. 11A
FIG. 11B
FIG. 11C
FIG. 11D
FIG. 11E
FIG. 11F
FIG. 11G
FIG. 11H

NON-CONTACT RAPID DIAGNOSIS OF ILLNESS BY LASER, INFRA RED, TERAHERTZ AND/OR UV SPECTROSCOPY AND ANALYSIS OF WATER MIXTURE ENVELOPE

This disclosure generally relates to rapid diagnosis of various illnesses (of people or animals) with non-contact spectroscopy by directing electromagnetic radiation such as a laser and/or infra red, terahertz and/or UV at a target subject and the area surrounding the target subject or at an Object (e.g., an Object such as water within the target subject's body and/or in the area surrounding the target subject's body) and analyzing a bodily emission of the target subject such as a water vapor emitted by the subject, in some embodiments with the assistance of a contrast material.

BACKGROUND

People obtain medical diagnoses for systemic conditions, for conditions of their organs by providing a sample. This requires taking an action with part of their body, such as positioning themselves and then opening their mouth or removing clothing and exposing part of their body to a physician or to an imaging machine, or turning their body to a certain side, position or orientation so as to make a particular organ accessible to a doctor or a machine. This also typically occurs through contact with the health care professional or the diagnostic machine.

SUMMARY OF THE EMBODIMENTS

It has not been possible to diagnose people without their active participation. Typically, this requires stopping and possibly removing clothing or at least providing a saliva or other sample. In airports or other situations in which large numbers of people who pass by need to be tested, as well as in any other medical setting, Applicant has determined that it would be advantageous to detect the medical conditions of the people, for example the passing by, without requesting a sample and without requesting their active participation or interaction. Even when a single individual is involved, it is advantageous to be able to diagnose a medical condition of the individual without a sample or other active participation by the patient.

Furthermore, different medical conditions typically require different diagnostic tests involving different diagnostic machines. While it is true that blood tests can reveal many things about a person's health, this requires the person's active participation over time in an invasive procedure in a controlled environment. In addition, blood tests take time, in fact usually days, to perform and analyze so as to then receive the results. Furthermore, blood tests require removing from the subject a valuable fluid of the human body (blood) and therefore cannot be repeated at liberty (i.e., constantly) without detrimental effect.

Applicant has discovered a way of non-invasively medically diagnosing a wide variety of medical conditions without the active participation of the subject.

One embodiment is a non-contact rapid diagnostic system, comprising:

water that has been treated electrochemically;

at least one frequency-stabilized laser device configured to generate and direct electromagnetic radiation of a wavelength in the UV range or in the visible light range at a subject and/or at an area surrounding the subject containing a water mixture envelope comprising a mist or sprayed form of the electrochemically treated water and a low disperse water envelope (LDWE) emitted from the subject's body;

a digital to analog converter configured to receive the reflected beam and generated a digitized reflected beam;

a digital processing unit configured to:

using a signal analysis algorithm, generate (i) a spectrogram from the digitized reflected beam or (ii) both the spectrogram and an image derived from the spectrogram, store reference spectra of healthy subjects and ill subjects on a non-transitory computer readable storage medium, each of the ill subjects suffering from one or more medical conditions, the medical conditions comprise brain hemorrhage, brain cancer and cancer of the pancreas the subject's body and find a first pattern of frequencies in the reference spectra of the healthy subjects and ill subjects based on one or more of an amplitude, phase shift, frequency shift and a chemical shift of frequencies in the reference spectra, wherein the reference spectra derive from one or more imaging techniques including PET CT, CT, MRI, and the frequency-stabilized laser scanning the brain or the pancreas;

derive a first pattern of concentrations of electrolytes and protein molecules in the stored reference spectra from the first pattern of frequencies using neural networks;

determine, after generating the spectrogram or both the spectrogram and the image, a second pattern of frequencies in a water spectra of the subject based on one or more of an amplitude, phase shift, frequency shift and a chemical shift in the water spectra of the subject, and derive a second pattern of concentrations of electrolytes and protein molecules in the water mixture envelope of the subject from the second pattern of frequencies using the neural networks;

compare the first pattern of concentrations with the second pattern of concentrations;

determine, based on the comparing of the first and second pattern of concentrations, at least a preliminary indication of whether the subject suffers from one or more of the variety of medical conditions by executing pattern recognition software; and output the determination.

In some embodiments, the one or more of a variety of medical conditions comprises cancer and wherein the second pattern of frequencies of the subject indicates a resonance density of at least seven.

In some embodiments, the digital processing unit creates an unsupervised training set from the references spectra of the healthy and ill subjects.

In some embodiments, the treated water is configured to act as a contrast material vis a vis the LDWE so as to increase a signal to noise ratio and thereby facilitate processing of the one or both of the spectrogram and the image of the reflected beam reflected from the laser device. In some embodiments, the reflected beam has an electromagnetic frequency of the reflected laser.

In some embodiments, the water mixture envelope comprises particles of 1-60 microns in diameter.

In some embodiments, the electromagnetic radiation comprises a laser beam having a range of wavelengths from 600 nm to 685 nm and wherein the laser device is configured to direct the laser beam.

In some embodiments, the system further comprises an infra red device configured to emit electromagnetic radiation having a wavelength from 1050 nm to 2900 nm.

In some embodiments, the system further comprises an infra red device and wherein the digital processing unit is configured to obtain (i) an external water fingerprint from a spectroscopic analysis of the one or both of the spectrogram and image from the reflected beam that was reflected from the electromagnetic radiation emitted by the laser device and (ii) a general water fingerprint of both the water mixture envelope external to the subject and of water internal to the body of the subject derived from signal from the reflected beam that was reflected from the electromagnetic radiation emitted by the infra red device, and to compare each of the external and general water spectra with the stored spectra.

In some embodiments, the system further comprises a terahertz device wherein the electromagnetic radiation that is emitted by the terahertz device has a frequency of 1.0·10^5 MHz to 1.0·10^7 MHz.

In some embodiments, the electromagnetic radiation emitted by the at least one laser device is non-ionizing UV radiation that has a wavelength of 320 nm to 385 nm.

In some embodiments, the one or more of a variety of medical conditions comprises cancer and wherein the digital processing unit is configured to perform a spectral analysis of an external water spectra and of a general water spectra to distinguish between healthy and ill subjects based on a magnitude of a resonance density.

In some embodiments, the system further comprises mirrors configured to mechanically adjust a beam of the laser device via an alignment of the mirrors, the laser device configured to be adjusted electrically by adjusting one or more of a frequency and a power of the laser device so as to select a depth of penetration of a laser beam into the water mixture envelope in order to scan different layers of the water mixture envelope.

In some embodiments, the system further comprises an infra red device positioned 2 to 5 meters from the subject.

In some embodiments, the at least one frequency-stabilized laser device comprises is a helium-neon laser device.

In some embodiments, a stability of the frequency-stabilized laser device is <7×10^−16 or is <1.5×10^−15.

In some embodiments, the water that has been treated electrochemically is water that has been treated by electrocoagulation and has been prepared by an electrochemical process that utilized an oxidative reduction potential (ORP) of between −800 mV and −400 mV.

Another embodiment is a method of non-contact rapid diagnosis of a subject, the method making use of a water Object associated with the subject, without active participation of the subject, the method comprising:

- discharging electrochemically treated water toward a low disperse water envelope (LDWE) emitted by the subject, the LDWE surrounding the subject so as to be within 5 meters of the subject, so as to form a water mixture envelope;
- transmitting electromagnetic radiation having a wavelength in the UV range or visible light range, using at least one frequency-stabilized laser device, toward the subject or an area surrounding the subject containing the water mixture envelope;
- using an analog to digital converter to receive a reflected beam and generating, using the analog to digital converter, a digitized reflected beam;
- executing instructions, by a digital processing unit, to perform:
  - using a signal analysis algorithm, generating from the digitized reflected beam (i) a spectrogram or (ii) the spectrogram and an image derived from the spectrogram;
  - storing reference spectra of healthy subjects and ill subjects on a non-transitory computer readable storage medium, each of the ill subjects suffering from one or more medical conditions, the medical conditions comprise brain hemorrhage, brain cancer and cancer of the pancreas, diabetes, a sexually transmitted disease and diseases caused by pathogens in the subject's body and finding a first pattern of frequencies in the reference spectra of the healthy subjects and ill subjects based on one or more of an amplitude, phase shift, frequency shift and a chemical shift of frequencies in the reference spectra, wherein the reference spectra derive from one or more imaging techniques including PET CT, CT, MRI, and the frequency-stabilized laser scanning the brain or the pancreas;
  - deriving a first pattern of concentrations of electrolytes and protein molecules in the stored reference spectra from the first pattern of frequencies using neural networks;
  - determining, using (i) the spectrogram or (ii) the spectrogram and the image, a second pattern of frequencies in water spectra of the subject based on one or more of an amplitude, phase shift, frequency shift and a chemical shift in the water spectra of the subject, and derive a second pattern of concentrations of electrolytes and protein molecules in the water mixture envelope of the subject from the second pattern of frequencies using the neural networks;
  - compare the first pattern of concentrations with the second pattern of concentrations;
  - determining, based on the comparing of the first and second pattern of concentrations, at least a preliminary indication of whether the subject suffers from one or more of the variety of medical conditions by executing pattern recognition software; and
  - outputting the determination.

BRIEF DESCRIPTION OF THE DRAWINGS

Various embodiments are herein described, by way of example only, with reference to the accompanying drawings, wherein;

FIG. 9A shows a spectrogram of a water mixture envelope surrounding or adjacent a normal hemisphere of a brain of a subject taken using a laser, in accordance with one embodiment;

FIG. 9B shows a graph of the amplitude over time derived from the frequencies of the spectrogram of FIG. 9A, in accordance with one embodiment;

FIG. 9C shows a spectrogram similar to FIG. 9A except that it is of the water envelope mixture surrounding or adjacent the pathological hemisphere of the subject's brain, in accordance with one embodiment;

FIG. 9D shows a graph of the amplitude over time derived from the frequencies of the spectrogram of FIG. 9C, in accordance with one embodiment;

FIG. 9E shows a spectrogram of a normal hemisphere of a brain of the subject (of FIG. 9A) taken using a laser, in accordance with one embodiment;

FIG. 9F shows a graph of the amplitude over time derived from the frequencies of the spectrogram of FIG. 9E, in accordance with one embodiment;

FIG. 9G shows a spectrogram of a pathological hemisphere of a brain of the subject (of FIG. 9C) taken using a laser, in accordance with one embodiment;

FIG. 9H shows a graph of the amplitude over time derived from the frequencies of the spectrogram of FIG. 9G, in accordance with one embodiment;

FIG. 11A shows a spectrogram of a water mixture envelope surrounding a normal portion of a pancreas of a subject taken using a laser, in accordance with one embodiment;

FIG. 11B shows a graph of the amplitude over time derived from the frequencies of the spectrogram of FIG. 11A, in accordance with one embodiment;

FIG. 11C shows a spectrogram of a pathological portion of the pancreas of the subject of FIG. 11A taken using a laser, in accordance with one embodiment;

FIG. 11D shows a graph of the amplitude over time derived from the frequencies of the spectrogram of FIG. 11C, in accordance with one embodiment;

FIG. 11E shows a spectrogram of a normal portion of the pancreas of the subject of FIG. 11A taken using a laser device, in accordance with one embodiment;

FIG. 11F shows a graph of the amplitude over time derived from the frequencies of the spectrogram of FIG. 11E, in accordance with one embodiment;

FIG. 11G shows a spectrogram of a pathological portion of the pancreas of the subject of FIG. 11C taken using a laser 32, in accordance with one embodiment;

FIG. 11H shows a graph of the amplitude over time derived from the frequencies of the spectrogram of FIG. 11G, in accordance with one embodiment;

DETAILED DESCRIPTION OF THE EMBODIMENTS

Figure 1B:
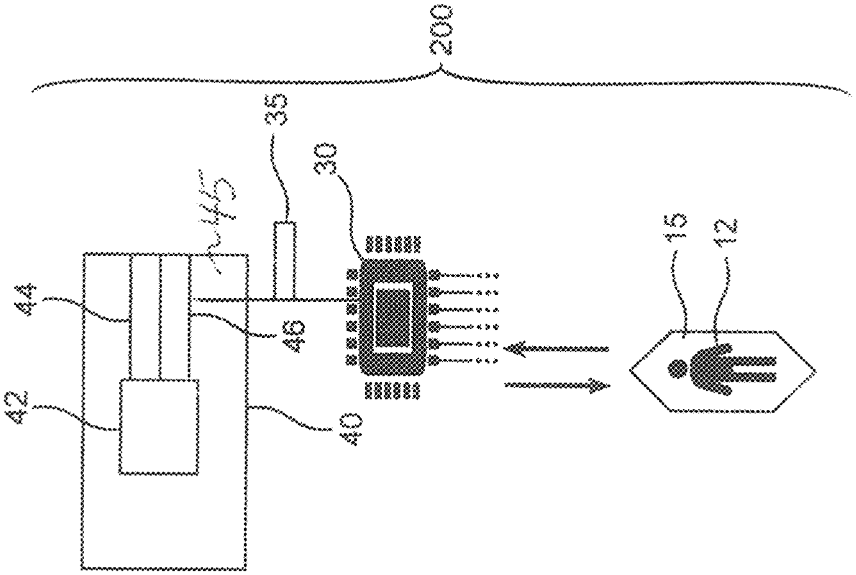
FIG. 1B is a schematic illustration of another system, in accordance with one embodiment.

Applicant has discovered a non-invasive non-contact system and method of rapidly obtaining a medical diagnosis of one or more of a wide variety of medical conditions, for example within a few seconds, or in some cases in real time, without the active participation of the subject and without taking or receiving samples from the subject.

Certain embodiments generally provide a system that may be used to diagnose one or a plurality of individuals without those individual(s) actively participating such as by providing a sample, orienting their body or a portion of their body or otherwise actively interacting with the diagnostic system or instruments.

Certain embodiments find a wide variety of applications in both medical and non-medical fields. Within the medical field, certain embodiments are applicable to medical diagnostics for a variety of illnesses and conditions. In the non-medical field, applications of the invention include detecting a person's physical and mental state of health for security purposes or military or other purposes. The figures illustrate one exemplary embodiment of a device or system for diagnosing a wide variety of medical conditions of a subject from afar without requiring the subject to take action. It will be appreciated that this example is only one of a large number of suitable applications for the technology, as will be clear to a person of ordinary skill in the art.

Applicant has come to appreciate that in the medical diagnosis field, a diagnosis made in less than a second is more valuable than one made in 2 days and even more valuable than one made in 3 hours. One non-limiting example that has been relevant over the recent years is the rapid diagnosis of a pathogen, for example Covid-19. The fastest reliable diagnoses of Covid-19 are currently about 3 hours. While this is an improvement over systems/devices/methods that require over a day, for airport security a day may be too late. At airports there are a lot of interactions between passengers waiting for a flight or preparing for checking in to a flight. Therefore, checking the infection status of each passenger the day before or even earlier the same day is not as helpful as their infection status as of the moment they enter the aircraft. However, even if someone is tested just before a flight, if the results are not known until three hours later, it may be too late since the passenger is already on the flight in an enclosed space with the windows unopenable. Accordingly, a rapid diagnosis of Covid-19 or another pathogen that takes less than one second is more valuable than a test whose results take even just 3 hours. Certain embodiments described herein do achieve a diagnostic output in less than a second.

In addition, Applicant has realized that a diagnostic test that requires stopping each passenger and performing an action such as a swab in several parts of the nose and mouth lengthens the preparation needed before the flight since an entire station manned by qualified people has to be inserted into the check-in procedure and each passenger has to stop to be checked. With all the already numerous check-in requirements, and the large number of passengers this is a burden. Accordingly, Applicant has realized that a diagnostic test that interrupts the flight check-in procedures and requires stopping each and every passenger is not as valuable as one that does not require any active human participation once the technical components are positioned in place. Certain embodiments are non-contact diagnostics that do not require the active participation of the subjects. In a typical setting, though, it may be appropriate that the subject (i.e., the target) be made aware that the diagnosis is occurring. Within a second or at most a few seconds, it can post the diagnostic output. For example, a board that has lights to light up regions of the board selectively can light up a number previously given to and associated with the passenger before passing through the diagnostic area. This way, the passenger is anonymously informed of the results of the test when for example they are waiting for the time of boarding the flight or even after.

In some embodiments, the system/method/device is configured to diagnose, or tentatively diagnose, many different medical conditions, including medical conditions that vary completely from one another, using the same diagnostic test. For example, in some embodiments, the diagnostic system can detect presence of a pathogen such as Covid-19 or a bacteria such as *Helicobacter pylori* (*H pylori*) but can also detect that a person has diabetes mellitus or cancer or a particular type of cancer or another illness, such as, but not limited to, a sexually transmitted disease such as gonorrhea or syphilis, or a disease of a particular organ. In some embodiments, the diagnostic system can detect a psychiatric condition such as a psychosis, depression or a neurodegenerative disorder such as dementia. These are non-limiting examples of a wide range of medical conditions or illnesses, both physical and mental, that the same test/diagnostic can identify (and hence diagnose).

As described in further detail below, the method/system comprises positioning a device, in one example a laser generating and emitting device, at an individual passing by a certain area. In one version, a wide room can have multiple lasers directing a beam of electromagnetic radiation from above and the side at different angles. In certain embodiments, some or all of the multiple lasers may be in constant modes or may be in pulsed modes, with the possibility of retuning in frequency, power and multidirectional modes (by polarization) in order to make sure that everyone who passes by the targeted area is identified by at least one laser. In another embodiment, one laser or two lasers are sufficient in a case where the people are requested or—by the nature of the surrounding structures-forced to temporarily walk single file through a relatively narrow area so that the laser or one of the two lasers directs its beam at each individual who passes. The laser beam may be configured to be directed at a bodily emission of the target individual being diagnosed.

In certain embodiments, the laser beam is reflected back to an analog to digital converter and then to a digital processing unit (containing spectral imaging programming instructions) configured to process the reflected beam of light reflected from the bodily emission of the individual who passes by into a spectrogram and optionally an image from the spectrogram. Examples of bodily emissions are the water vapor emitted by each individual through the skin and the water vapor exhaled from the lungs through the mouth and nose. However, as explained more particularly below, the amount of water vapor need not be large and therefore a part of the body covered by clothing can in some embodiments be considered "exposed" to the shining of the laser also. The system may further comprise a conversion device configured to convert an analog version of the electromagnetic vibration frequency of the reflected beam to a digital version of the electromagnetic vibration frequency. A digital processing unit may be configured to perform a spectroscopic analysis on the digital version of the electromagnetic vibration frequency of the reflected beam and to output at least a tentative diagnosis of a medical condition of the target subject.

Figure 4:
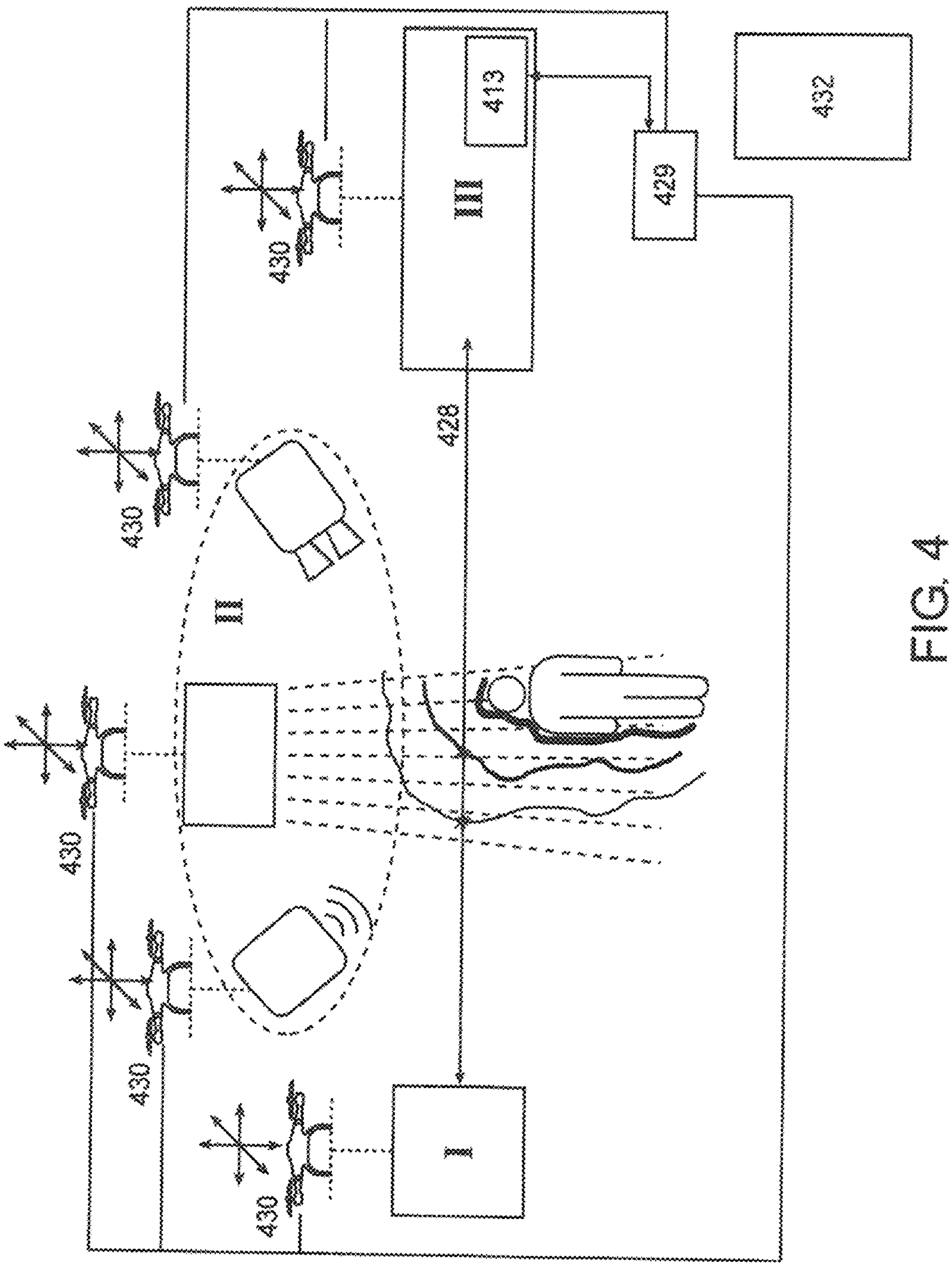
FIG. 4 is a generalized schematic illustration of a generalized version of the system of FIG. 3 utilizing drones, in accordance with one embodiment.

In some embodiments, as shown in FIG. 4, one of the options for housing components of the system for non-contact research is the use of mobile containers/chambers in the form of at least two drones (for example octo drones) or micro aircraft of similar properties. One drone may be equipped with at least one helium-neon frequency stabilized laser with a laser guidance and stabilization system in flight. The other drone may be equipped with at least one reflective element with a precision multi-coordinate adjustment system, for example including stepper electric drives, piezoceramic and thermal drives of the reflective element with a stabilization system (electromechanical and software with separation of unnecessary signals due to the operation of the drone) of the reflective element during flight. The drones may be integrated by means of a single control system (for example artificial intelligence or AI engineering) that may be configured to guarantee an optical location of the laser radiation source and the reflective element during full or partial scanning of the outer aqua shell (envelope) of the target subject. In some implementations the drones are not closer than 1.5-3 meters from the target subject under study. This is sometimes referred to herein as DADST (Distance Adjustable Drone Scanning Technology).

Although people exhale and produce a combination of water vapor and carbon dioxide through their mouth and nose, Applicant has determined that not only during active physical exercise do people produce useful bodily emissions such as water vapor, but even a person sitting or even lying down produces useful body emissions such as water vapor.

The object of research and measurement in our method is water vapor around the human body in exhalation and at a distance of about 1 meter from the surface of the skin. Under normal conditions, the absolute humidity (mass of water vapor per unit volume) in the exhaled air can be approximately 40 to 50 $g/m^3$. The partial pressure of the water vapor in the exhaled air can reach about 6% of the total air pressure, which at standard atmospheric pressure (1013 mbar) is about 60 mbar. The evaporation of water through human skin, known as transepidermal water loss (TEWL), which averages for adults range from 300 to 400 $g/m^2$/day (grams per square meter per day).

In order to obtain biologically significant information from such an aquashell (the term "aquashell" referring to the continuous shell of water vapor surrounding the human body), in some embodiments, a contrast material is used comprising finely dispersed sprayed specially prepared water depending on the task with the following characteristics: ORP from +400 mV to −850 mV, PH from 4.5 to 9, regulated concentration of deuterium atoms (in some cases tritium). In some embodiments, depending on the task, quantum dots are also used.

The principles and operation of a Non-Contact Rapid Diagnosis of Illness by Laser, Infra Red, Terahertz and/or UV Spectroscopy and Analysis of Water Mixture Envelope may be better understood with reference to the drawings and the accompanying description.

Turning now to the non-limiting example shown in FIGS. 1-6, FIG. 1A shows a schematic version of a non-contact rapid diagnostic system 10. System 10 may comprise treated water 20, that is specially prepared water that has been treated to remove impurities. In some embodiments, this water is electrochemically treated water, for example using an electrochemical method to remove impurities from the water. In one example, the electrochemically treated water is electrochemically treated waste water.

This electrochemical treatment may also be accompanied by adjusting or re-ordering the hydrogen bond grid (H-grid, H-grid) of the treated water 20. This adjustment may occur by controlling the oxidative reduction potential (ORP), which without such control may vary anywhere from plus +800 to minus (−) 850 millivolt (mV), and in some cases may depend also on controlling a variation in the pH, which may vary from 4.5 to 10 (or from 4.5 to 9). Furthermore, this treatment may also involve the addition of certain chemical indicators, for example indicators that change color in the presence of various metabolites in the body of healthy and sick subjects.

Applicant has also found that treating water to remove impurities, for example wastewater impurities, is very useful for later use during imaging (in accordance with certain embodiments of the systems and method described herein) of a mixture 16 of the treated water 20 or purified water 20 and a low disperse water envelope 15 that has been emitted (and is being emitted) from a mammalian subject. In that case, the treated water 20 functions as a contrast material.

Applicant has found that the effectiveness of the treated water 20, for example electrochemically treated water 20, as a contrast material is optimized in some embodiments, by keeping the oxidative reduction potential (ORP) in the negative range as close as possible to the range from −70 mV to −150 mV during the electrochemical treatment for preparation of the treated water 20. The contrast material may form a contrast vis-à-vis other water, in particular water emitted by a target subject's body in the natural course of events, as part of a mixture of both the contrast material and the emitted water. The emitted water may form a low disperse water envelope (LDWE) 15 surrounding the target subject 12 or the target subject's body 12. In some embodiments, the droplet size of the sprayed treated water 20—including when it is mixed into the water mixture envelope 16—is in the range of 1-100 μm ("μm" refers to micrometers or microns). The emitted water may refer to water emitted through the target subject's skin (transdermally), through the target subject's nose and/or through their mouth (or through the target subject's anus). Typically, this emitting of the water occurs without any special effort or intent by the target subject. The water within the target subject and the area surrounding the target subject (water mixture envelope) may each also be referred to as the "Object" or the "water Object" since it is the water within or surrounding the target subject that is targeted, in accordance with certain embodiments herein.

The Object of measurement in the systems and methods described herein is water vapor around the human body arising from exhalation (or transdermally) and at a distance of about 1 meter from the surface of the skin. Under normal conditions, the absolute humidity (mass of water vapor per unit volume) in exhaled air can be approximately 40 to 50 $g/m^3$. The partial pressure of the water vapor in the exhaled air can reach about 6% of the total air pressure, which at standard atmospheric pressure (1013 mbar) is about 60 mbar. The evaporation of water through human skin, known as transepidermal water loss (TEWL), averages for adults range from 300 to 400 $g/m^2$/day (grams per square meter per day). In order to obtain biologically significant information from such an aquashell (a continuous shell of water vapor) surrounding the individual target, in some embodiments, the water from the target's body is mixed with a contrast material that may comprise a finely dispersed spray of specially prepared water. In some embodiments, the specially prepared water has an ORP from +400 mV to −850 mV and a PH from 4.5 to 9. In some versions, this specially prepared or treated water 20 may have regulated concentration of deuterium atoms (in some cases tritium).

Applicant has conducted extensive experiments over the past decade on at least one human individual using a system that incorporates helium-neon gas frequency-stabilized lasers in combination with a laser polarimeter and an infrared camera. The experiments included obtaining biologically significant information about the individual and comparing doing so in a case where specially treated water 20 is sprayed with a case in which no specially treated water 20 is used. It was found that use of the sprayed specially electrochemically treated water 20 as contrast material resulted in obtaining much more biologically significant information.

Regarding the treated or purified water 20, Applicant has discovered that treatment of water electrochemically, for example through electrocoagulation, is a very effective way of obtaining treated water 20 that is effective for use as the contrast material. The use of the contrast material has been found to improve the signal to noise ratio that is obtained when electromagnetic radiation strikes the mixture of the emitted water surrounding the subject (low disperse water envelope) and the treated water 20 (i.e., electrochemically treated water or electrocoagulated water).

In some embodiments, the treating of the water includes pre-treatment and/or reverse osmosis and/or bidistillation followed by electrocoagulation with various electrodes (soluble and insoluble), and may include one or more of electroflotation, separation and discharge of the coagulant, subsequent cleaning from residues of coagulant and optionally mixing chemical reagent indicators.

In certain embodiments, the preparation of the treated water 20 using an electrochemical process utilizes an ORP of about −70 mV or about −150 mV or an ORP that is as close to this range as possible in order to optimize the effectiveness of the treated water 20 as a contrast material during later imaging. For example, in some embodiments the treated water 20 is prepared through an electrochemical process such as electrocoagulation that utilizes an amount of ORP that varies within the range of 0 to −200 mV or −50 mV to −200 mV, or −150 mV to 0 mV or 0 mV to −250 mV, or 0 mV to −300 mV or 0 mV to −400 mV, or from −200 mV to 0 mV or 0 to −100 mV. Each range is a separate embodiment. It is also noted that the electromagnetic radiation used herein, including coherent radiation in the range from the visible to the long infrared and terahertz range, is non-ionizing radiation.

Figure 1A:
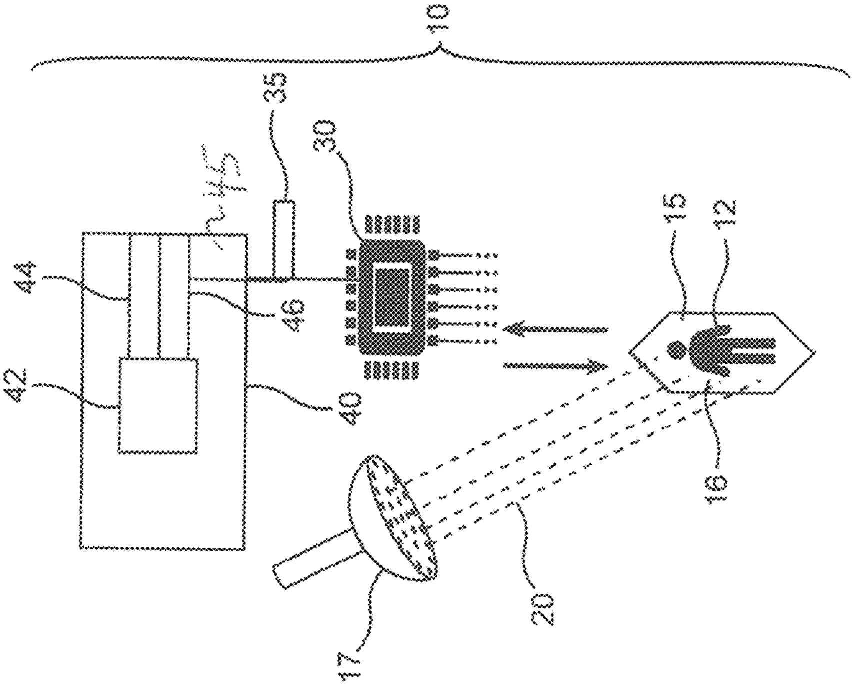
FIG. 1A is a schematic illustration of a system, in accordance with one embodiment.

In one embodiment shown in FIG. 1A, treated water 20, i.e., water treated by removal of impurities, for example by electrochemical processes such as or including electrocoagulation (such treated water 20 sometimes referred to as electrocoagulated water), is delivered to the water envelope 15 surrounding the target human subject 12 for mixture therewith. Applicant has tested a delivery method that involves spraying the treated water 20, for example the electrochemically treated or electrocoagulated water 20, toward the target subject 12 or toward the envelope 15 surrounding the target subject 12, and found this delivery method to be effective in creating an effective contrast material for later imaging. In this delivery method, the treated water 20 is delivery by being sprayed or ejected as a mist. For example, the treated water 20 may be held in a suitable container or device and then ejected in a spray or mist form toward the target subject 12 and/or toward the water envelope 15 surrounding that target subject 12. In one version, a water spray control system 17 comprises multiple spray devices, that may or may not be overhead devices, and that may deliver the treated water 20 to the water envelope 15 surrounding the one or more target subject's body. As seen in FIG. 1A, this control system 17 may be pre-positioned to squirt or spray the treated water toward one or a group of target subjects 12 moving or walking in a certain direction, for example moving single file through a narrow pathway. This orientation or position of the subject(s) is merely exemplary—the subject or subjects may also be situated in other positions or orientations. The target subject 12 or target subjects 12 may for example be sitting, lying down, standing, walking or positioned in some other position, preferably one that allows the water envelope 15 surrounding their body, or surrounding a portion or at least a portion of their body that is of interest, to be exposed to the electromagnetic radiation. Each position or orientation described is a separate embodiment.

In some embodiments, the treated water, in spray or mist form, has particles that are small, namely in the range of 20-50 microns. The use of the treated water 20 that is sprayed or in mist form as a contrast material enhances the signal to noise ratio of the signals that are obtained upon use of the at least one device 30. This increases by approximately 10-15 times the reflection coefficient of the signal obtained.

In some embodiments, the laser device 32 and/or the infra red device 34 is positioned from two to five meters from the target subject 12. In other embodiments, the laser device 32 and/or the infra red device 34 is positioned at a distance greater or less than 2-5 meters. In some embodiments, the laser device 32 is a helium-neon laser device 32. The laser device 32 and/or the infra red device 34 may include a transmitter and a receiver.

In one embodiment of system 10 or systems 200, 300, 400, the at least one device 30 comprises a frequency-stabilized laser device (defined as a laser defined that has the ability to keep their frequency over time with limited fluctuations), for example a frequency-stabilized laser device whose stability is <7×10^−16. In another embodiment, the at least one device comprises a frequency-stabilized laser device whose stability is <1.5×10^−15. Each option is a separate embodiment. Stabilization of the frequency of the laser beam may be achieved using the methods and techniques described in the books and articles known to those skilled in the art. In some embodiments, a frequency-stabilized laser device, for example an ultrastable laser, may be purchased from Menlo Systems, a company based in Martinsried, near Munich, Germany, at www.menlosystems.com. The use of a frequency stabilized laser results in a more precise diagnosis by system 10, system 200, system 300, system 400, method 100. This is because if the frequency of the laser does fluctuate too much, the analysis of the results can be less accurate. The use of a frequency-stabilized laser, for example an ultrastable laser, improves the signal to noise ratio of the resulting signal.

Furthermore, Applicant has discovered that the presence of clothing worn by the subject does not prevent the effective use of the system 10, 200, 300, 400, method 100. In the event that the clothing is very thick such as a thick winter overcoat, then in some embodiments, the subject may be asked to remove it. Fundamentally, though, it does not matter whether the target subject is dressed or not, with the exception of certain special clothing that shields infra red radiation and prevents the formation of a water envelope. An example of this would be fur coats, space suits or other clothing that is more than 4-5 cms (centimeters) thick.

Figure 6A:
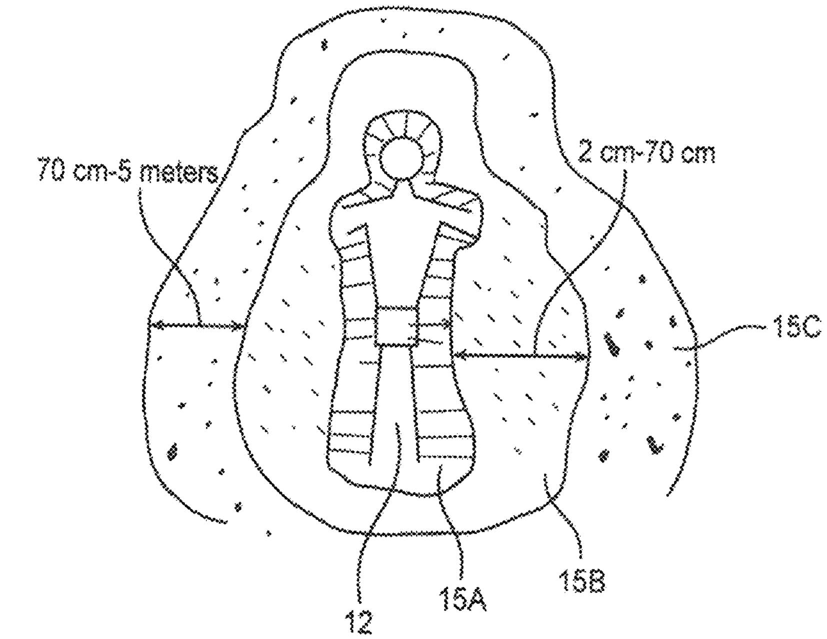
FIG. 6A is a schematic illustration of a water envelope (LDWE) surrounding the subject, in accordance with one embodiment.

In one implementation, the water envelope itself may have three degrees of separation from the source of the water, namely the subject's body. As shown in FIG. 6A, the first layer 15*a* may be considered that which is closest to the skin, namely from 0.1 mm from the subject's skin (or from the subject's skin itself) to 20 mm from the subject's skin all around the target subject's body. The second layer 15*b* of the envelope may extend from 2 cm to 70 cm. The third layer 15*c* of the envelope 15 may extend from 70 cm to 5 meters. As shown in FIG. 6A, these layers may be akin to layers of an onion in the sense that each layer surrounds the entire body of the subject and the adjacent layer surrounds the entire preceding layer. These divisions of the water envelope 15 represent one version and other divisions are possible. It is noted that after the treated water 20 is delivered/sprayed to the water envelope 15, the various layers 15*a*, 15*b*, 15*c* of the envelope 15 continue to carry over to the water mixture envelope 16 depicted in FIG. 6B as well. That is, one can describe layer 15*a* of the LDWE 15 shown in FIG. 6A as corresponding (in location) to a layer 16*a* of the water mixture envelope 16 shown in FIG. 6B and similarly layer 15*b* of the LDWE 15 corresponds (in location) to layer 16*b* of the water mixture envelope 16 and layer 15*c* of the LDWE 15 corresponds (in location) to layer 16*c* of the water mixture envelope 16). Layer 16*c* is sometimes referred to as a condensate layer.

In general, in any embodiment, the LDWE 15 and the water mixture envelope 16 may act as an extension of the subject's body such as a living organ that is an extension of the subject's body. In some embodiments, the images obtained of the water mixture envelope 16 (or of the low disperse water envelope (LDWE) 15) may be dynamic video images, in one non-limiting example a hologram or holographic images from video cameras, such as infra red video cameras or terahertz video cameras. In some embodiments, the video cameras are very sensitive or high speed video cameras such as 500-1000 frames per second.

Without being bound by theory, Applicant has found (with respect to any embodiment of the system 10, 200, 300, 400 or method 100 herein) that the LDWE 15 and the water mixture envelope 16 exhibit movements or flow that represent manifestations of activity with the body of the target subject 12. Without being by bound by theory, it may be that one movement or flow of the LDWE 15 or mixture 16 is directly connected to and corresponds to the pulsations of the heart of the subject 12. In that case, during the systolic phase of the heart pumping cycle when the heart contracts, the LDWE 15 or water mixture envelope 16 expands. Likewise, during the diastolic phase of the heart pumping cycle the heart expands and the LDWE 15 or water mixture envelope 16 contracts. Thus, the pulse-like flows of the LDWE 15 or water mixture envelope 16 surrounding the subject 12 may correspond to the heart pulsations of the subject 12 and provide information about the condition and health of the heart of the subject. Without being bound by theory, these pulsations also generate frequency shifts akin to Doppler effect.

However, the heart is not the only source of the flow movements within the LDWE 15 or within the water mixture envelope 16. Other movements of the LDWE 15 and water mixture envelope 16 include Brownian motion, circadian rhythm and other vibrations unconnected to the heart of the subject 12. A deceased subject's water mixture envelope 16 will still exhibit motions since as stated some of the source of the motions or flows are unconnected to the heart of the subject.

As shown in FIG. 1A, system 10 (and this is also true with respect to systems 200, 300, 400) may also include at least one device 30 that is configured to direct electromagnetic radiation at a subject 12 and/or at an area (e.g., the area occupied by water envelope 15) surrounding the subject containing a water mixture envelope comprising the sprayed or atomized or mist form of the treated water 20 and the low disperse water envelope (LDWE) 15 emitted from the subject's body 12. The water mixture envelope 16 may be transparent so as to not be disturbing for the target subjects.

The at least one device 30, in some embodiments, may comprise at least one of a (or more than one of a) laser device 32 configured to generate and direct electromagnetic radiation at the target subject (and/or the target subject's water envelope) and one or more infra red devices 34 configured to generate and direct electromagnetic radiation at the target subject (and/or at the target subject's water envelope). In certain embodiments, the one or more laser device or other device 30 may be guided by partially passing the laser beam through a polarization splitter to a polarimeter and a photodetector (CCD array), so as to completely or partially scan the scanned volume surrounding the target subject, while matching corresponding values of deflection angles of the adjustable mirror(s). In some cases, the at least one laser or infrared device include may include mirrors, dividers, expanders, CCD matrices, at least one laser in terahertz range, and may include a set of Electromagnetic Pulse (EMP) sources (coherent and incoherent, pulsed and constant) for greater contrast.

As shown in FIG. 1A and FIG. 1B, system 10 (and system 200) may include an analog to digital converter 35, and may also include spectral imaging software (or programming instructions) 45 that is part of the processing unit 40 and is configured to receive a digitized version of the reflected beam (of light having an electromagnetic frequency) reflected from the water mixture envelope 16 (and in some cases back to the laser device 30) and to convert the reflected beam (reflected from the water mixture envelope 16 that is a mixture of the treated water 20 and the emitted water envelope (LDWE) 15), for example using a Fourier transform or other signal analysis algorithm, to a spectrogram or to an image from the spectrogram. Analog to digital converter 35 can also be inside the digital processing unit 40.

The treated water 20 may be configured to act as a contrast material vis a vis the LDWE so as to facilitate processing of the one or both of the spectrogram and image of the reflected beam reflected from the laser device 32.

In some embodiments, the at least one device 30 comprises a laser device 32 and the electromagnetic radiation comprises a laser beam having a frequency of having a wavelength in the visible light range of 600 nanometer (nm) to 685 nm, which corresponds approximately to a frequency of 4.3765·10^8 MHz to 5·10^8 MHz.

In some embodiments, the at least one device 30 comprises an infra red device 34 and the electromagnetic radiation that is emitted by the infra red device 34 has a wavelength of 1050 nm to 3500 nm which corresponds to a frequency of approximately 8.5654988·10^7 MHz to 2.855·10^8 MHz. In some embodiments, the at least one device 30 comprises an infra red device 34 and the electromagnetic radiation that is emitted by the infra red device 34 has a wavelength of 1050 nm to 2900 nm, which corresponds to a frequency of approximately 1.033767·10^8 MHz to approximately 2.855·10^8 MHz. In some embodiments, the at least one device 30 comprises one or more laser devices 32 and one or more infra red devices 34.

In one implementation of system 10, the at least one device 30 is a frequency-stabilized laser device 32 emits electromagnetic radiation in the ultraviolet red and infrared ranges that is configured to emit non-ionizing low power UV radiation that has a wavelength of 320 nm (corresponding to 9.3685·10^8 MHz) (or a wavelength in the range of UV light, for example 220-420 nm). In another implementation, laser device 32 is a frequency stabilized laser device and is configured to emit light having a wavelength of 532.8 nm (or in the range of 400-700) (which is visible light). The emitted electromagnetic radiation and actively excites the particles in the LDWE to emit radiation.

The UV or other electromagnetic radiation directed by the laser device 32 at the water mixture envelope (or at the LDWE) surrounding the subject impacts the particles in the water mixture envelope (or at the LDWE). These particles, which may be particles of electrolytes (defined herein as sodium, potassium, calcium, and magnesium) or proteins that were emitted transdermally or through the subject's breath or through other apertures of the subject's body as described herein, oscillate electromagnetically. For example, evaporated perspiration contains such particles. The treated water 20 that was sprayed and which forms part of the water mixture envelope is configured to improve the signal to noise ratio of the reflected signal. In addition, the fact that the laser device 32 may be frequency-stabilized also improves the signal to noise ratio.

The particles mixed with the water vapor in the subject's water mixture envelope differ from one another in that some are organic (i.e. protein) and some are inorganic (i.e. electrolytes sodium, potassium, calcium and magnesium) and these differences affect their electromagnetic properties. For example, the different types of particles have different polarizations (inorganic electrolytes do not typically exhibit polarization (for example, sodium has a relatively low electronegativity and tends to lose its outer electron easily, resulting in a stable cation form) whereas proteins such as amino acids do exhibit polarization due to the distribution of charges along their phosphate-sugar backbone and the nitrogenous bases). The different types of particles also have different precession or spin characteristics. In addition, each electrolyte (sodium, potassium, calcium, magnesium) has a different external hydrogen bonding structure (lattice). Furthermore, the hydrogen bonding interactions of a protein molecule such as an amino acid differ from the hydrogen bonding interactions of an electrolyte, which leads to their having different resonance densities and different patterns of frequencies.

If a particular subject has x concentration of sodium and y concentration of potassium and z concentration of calcium and xx concentration of magnesium and yy concentration of a certain amino acid etc., then that subject's water mixture envelope will also have a particular collection of concentrations. Accordingly, that subject's water spectra (of the water mixture envelope) as determined by the spectral imaging software (or programming instructions) 45 that is part of the digital processing unit 40 will have one particular pattern of frequencies, resonance densities, amplitudes, amplitude shifts, phase shifts, chemical shifts, etc. in their spectra that differs from that of another subject with a different pattern of concentrations (in the electrolytes and proteins). Furthermore, in some implementations, parallel spectral (or hyperspectral) imaging technology is utilized in system 10 to obtain separate images of the different electrolytes and proteins, which are then processed by the digital processing unit 40.

After the emitting of the electromagnetic radiation at the particles in the water mixture envelope or in the LDWE, as a result of the receiving of the reflected beam, after being digitized by an analog to digital converter 35, the spectral imaging software (or programming instructions) 45 of the digital processing unit 40 is able to obtain an image, for example using Fourier transforms or other signal analysis algorithms, and the digital processing unit 40 is configured to determine the pattern of concentration of proteins and electrolytes (sodium, potassium, calcium and magnesium) in the water mixture envelope or LDWE, for example using Artificial Intelligence (AI) and/or neural networks, for example by unsupervised learning and/or supervised learning. Accordingly, the types of particles can be identified by these characteristics and their concentration in the water mixture envelope and/or in the LDWE may be used to define a signature for that subject's LDWE, and hence for that subject. The "signature" is what has been referred to herein in this patent application as the "fingerprint" or "water fingerprint". Accordingly, a specific pattern of concentrations of electrolytes and protein molecules in the water mixture envelope of the subject can establish a signature (i.e. fingerprint) of the water mixture envelope of the subject that would be reflected in the water spectra of that subject.

Figure 6B:
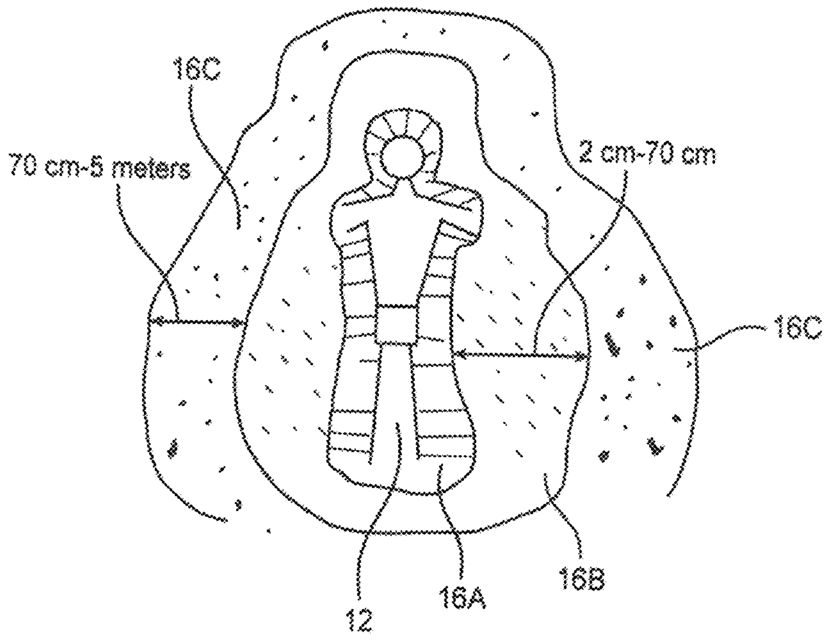
FIG. 6B is a schematic illustration of a water mixture envelope surrounding the subject, in accordance with one embodiment.

In one non-limiting example, by comparing reference spectra of healthy and ill subjects with spectra of the subject, preliminary or tentative diagnoses can be made of the subject's condition. For example, electrolyte imbalances and abnormal presence or abnormal quantities of proteins in the water mixture envelope and/or in the LDWE are associated with diseases. For example, using unsupervised learning, the digital processing unit 40 with machine learning software can find patterns of concentration of proteins and electrolytes in the water mixture envelope (or LDWE) of reference subjects, for example from the reference spectra of healthy subjects and ill subjects, and may create an unsupervised training set. Then, in order to compare the pattern of concentrations of the electrolytes and proteins in the water mixture envelope (or LDWE) of the subject with that of the ill subjects and healthy subjects, the digital processing unit 40 may utilize supervised learning and may create a supervised training set. In some embodiments, laser device 32 may be configured to be adjusted at least one of mechanically and electrically. For example, the laser device 32 may be configured to be adjusted mechanically the beam emitted by the laser device via an alignment of mirrors and/or is configured to be adjusted electrically by adjusting one or more of a frequency and a power of the laser device 32. The mechanical adjustment and/or the electrical adjustment are configured so as to select a depth of penetration of the laser beam into the water mixture envelope 16 (the mixture of the low disperse water envelope 15 (LDWE) and the treated water 20) in order to scan different layers of the water mixture envelope 16 (FIG. 6B).

Regarding the mechanical adjustment of the beam emitted by the laser device 32, this adjustment uses mirrors (for example mirrors 403, 404 in FIG. 3) and involves the one or more processors 42 executing an algorithm to stabilize the frequency of the laser device 32, wherein a distance between the mirrors in the laser cavity is precisely adjusted (with a thermal drive) using this algorithm to stabilize the frequency. The algorithm positions reflecting mirrors (not the mirrors in the resonator), directing part of the scanning laser beam back into the laser cavity and part to the laser polarimeter. These are completely different mirrors than those in the resonator.

As a result of the conjugate mirrors, the spectral imaging software (or programming instructions) 45 of processing unit 40 obtains a dynamic Fourier image (or a dynamic image from another signal analysis algorithm) of the scanned volume, as well as a dynamic polarization image of the scanned volume of the LDWE. Without being bound by theory, Applicant states that this dynamic Fourier image (or other dynamic signal analysis) and dynamic polarization image carry a cumulative reflection of the functional state of the subject because: A) biomolecules (for example proteins such as DNA, RNA, etc.) in aqueous solutions are capable of modulating electromagnetic radiation; and B) due to quantum effects in biological systems. Without being bound by theory, Applicant notes that an article by Chen called "Quantum Biology" in the publication Nature Physics 9, 10-18 (2013), and published at www.nature.com, which is incorporated by reference in its entirety, discusses quantum effects in biological systems.

Regarding the neural networks that are used by the digital processing unit 40 to determine or derive the pattern of concentration of proteins and electrolytes (sodium, potassium, calcium and magnesium) in the water mixture envelope or LDWE of the stored reference spectra for any method or system herein, the neural networks may be trained on (A) one or more highly regarded (by the medical profession or scientific community) and well-established imaging techniques including PET CT, CT, MRI of the subjects and in particular such imaging of the same organ of the same subject (whose adjacent or surrounding water envelope mixture is scanned by the frequency-stabilized laser scanning and processing of one of the methods or systems described herein and whose tentative diagnosis or evaluation is being sought by one of the methods or systems described herein), examples of which are shown in FIG. 10A, FIG. 10B, FIG. 12A and FIG. 12B and/or on (B) the frequency-stabilized laser scanning of the same subject, in particular of the same organ of the same subject, which means of the organ itself rather than of the water mixture envelope surrounding such organ of the subject, examples of which are FIG. 9E, FIG. 9F, FIG. 9G, FIG. 9H, FIG. 11E, FIG. 11F, FIG. 11G and FIG. 11H.

The database for training the neural networks may also include one or more of:

Photos and videos of high-speed video cameras from microscopes (electronic, laser) scanned samples (aqueous preparations of DNA molecules, RNA, as well as hormones, peptides and other biologically significant molecules)

Photo and video of water crystals processed by radiation signals from the frequency stabilization system when scanning samples of aqueous preparations of DNA and RNA molecules, as well as hormones, peptides and other biologically significant molecules with a frequency-stabilized laser Spectra of DNA molecules, RNA, as well as hormones, peptides and other biologically significant molecules Polarization Image of the Scanned Sample Speckles, especially dynamic speckles obtained with lasers of various ranges including infra red, ultra violet (samples of individual molecules of DNA or RNA or parts thereof or peptides or hormones. Speckles are a specific phenomenon associated with the interference of coherent light (e.g., a laser) scattered or reflected from microscopic irregularities of a surface (especially surfaces that move or change such as biological tissue). Each area of the surface results in the reflection or scattering of light with different phases, which forms a characteristic grainy structure. As a result of the interference, a random, granular pattern called a speckle field occurs. In our method and system, speckle acquisition is necessary to reinforce neural network training, improve the accuracy of analysis and diagnostics, and create auxiliary databases for training and express diagnostics.

Figure 2A:
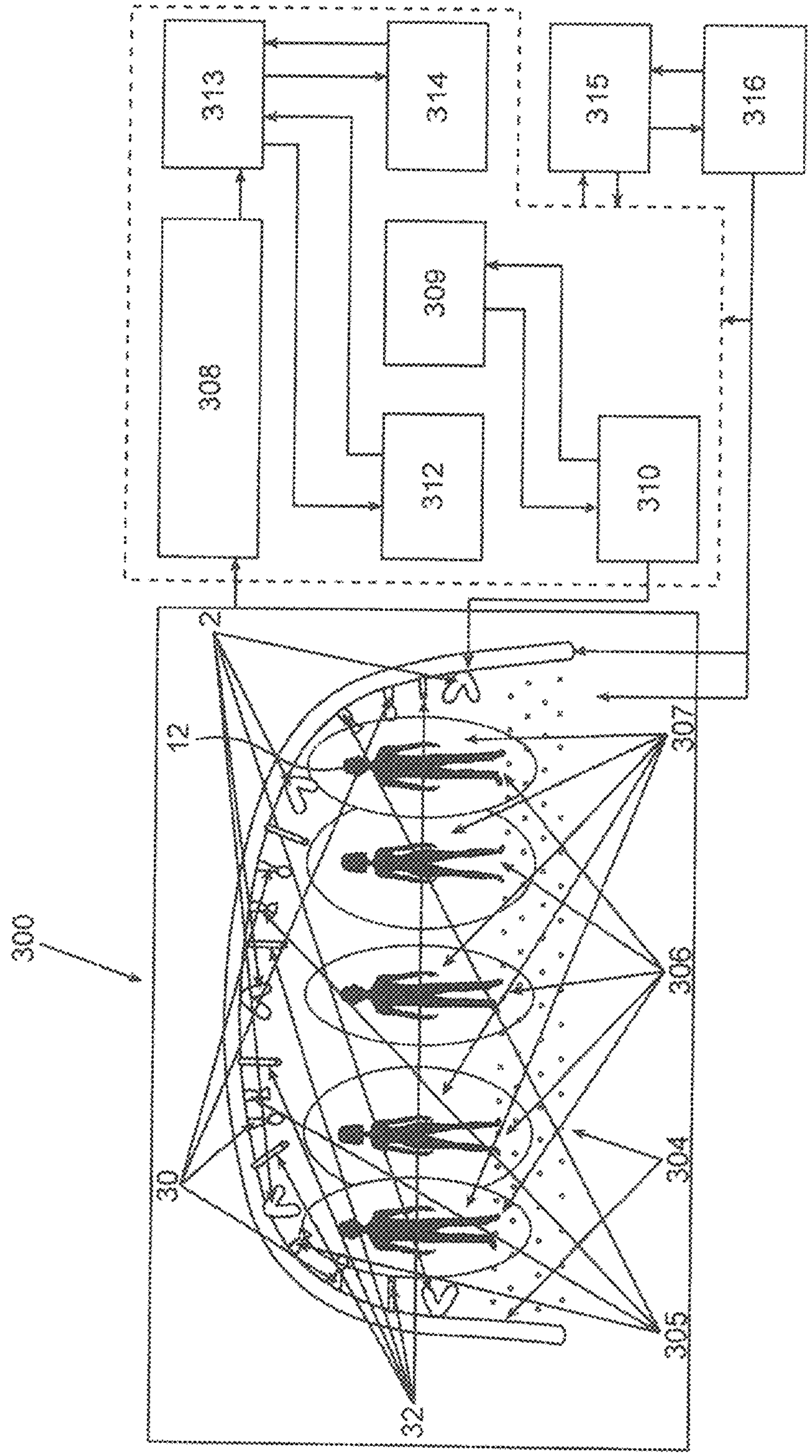
FIG. 2A is a graphic illustration of portions of a system along with a block diagram showing a workflow, in accordance with one embodiment.
Figure 2B:
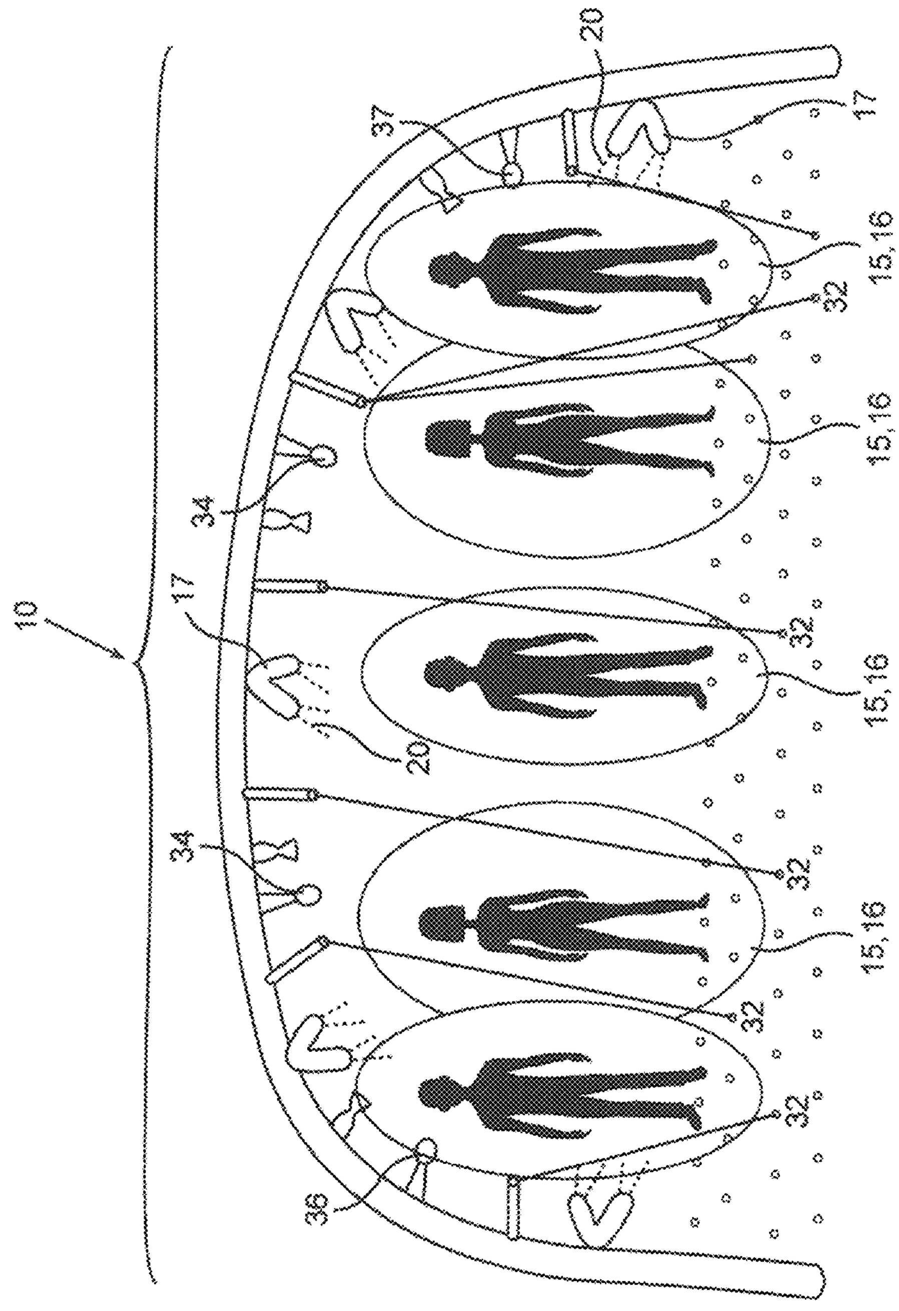
FIG. 2B is a graphic illustration of portions of a system, in accordance with one embodiment.

In some embodiments, as shown in FIG. 2B, the at least one device 30 is a continuous laser device 32. In other embodiments, the at least one device 30 is an impulse laser device 32.

In some embodiments, as shown in FIG. 2B, the at least one device 30 is a device configured to generate and direct electromagnetic radiation having terahertz frequency. The electromagnetic radiation that is directed at the subject and/or at the area surrounding the subject containing the water mixture envelope comprising the mist or sprayed or atomized form of the treated water 20 and the low disperse water envelope (LDWE) 15 may be provided by a device 30 that is called a terahertz laser device 36 or by a terahertz device 36 that is not called a laser device. The electromagnetic radiation emitted by device 36 may be terahertz radiation having a frequency of 0.1 to 10.0 THz, which is from 10^5 MHz to 10^7 MHz (approximately 30,000 nm to approximately 3,000,000 nm).

In some embodiments, as shown in FIG. 2B, the at least one device 30 is a continuous terahertz laser device 36 (or a continuous terahertz device 36) configured to generate and direct electromagnetic radiation in the terahertz frequency range. In other embodiments, the at least one device 30 is an impulse terahertz laser device 36 (or an impulse terahertz device 36) configured to generate and direct electromagnetic radiation in the terahertz frequency range.

In some embodiments, as shown in FIG. 2B, the at least one device 30 is a device 37 configured to generate and direct near UV radiation that is non-ionizing low power UV radiation. Device 37 may be configured to direct the non-ionizing low power UV electromagnetic radiation at the subject and/or at the area surrounding the subject containing the water mixture envelope 16 comprising the mist or sprayed or atomized form of the treated water 20 and the low disperse water envelope (LDWE) 15 (or at a water Object such as the water content within or surrounding the subject). In some embodiments, the near UV radiation (non-ionizing low power UV radiation) has a wavelength of 320 nm to 385 nm, which corresponds to a frequency range of approximately 7.7868·10^8 MHz to approximately 9.3685·10^8 MHz. In some embodiments, the UV radiation has a wavelength of 320 nm to 335 nm, which corresponds to a frequency of 8.949·10^8 MHz to 9.3685·10^8 MHz. In general, the different devices 32, 34, 36, 37 shown in FIG. 2B are non-limiting examples of implementations of the at least one device 30.

In general, a continuous laser device 32 requires more frequency stabilization that an impulse laser device 32.

System 10 may include a digital processing unit 40. The digital processing unit 40 of system 10 (and likewise of systems 200, 300, 400 or method 100) may be positioned locally or remotely and may include memory or memory storage 44 that stores program instructions 46 such as software 46 executed by one or more processors 42. The program instructions, in some embodiments, are executable by the digital processor so as to store reference spectra, for example of healthy target subjects and of ill target subjects on the memory 44. The ill target subjects are defined such that each of the ill target subjects suffers from or has one or more of a variety of medical conditions. The reference spectra may be obtained by directing at least one device 30 (laser device 32 and/or infra red device 34) at people known to be without a medical condition and at people who are known to have a specific medical condition, and the data collected and stored on memory 44.

In some embodiments of any of the systems (10, 200, 300, 400) or methods described herein, the variety of medical conditions comprise one or more of cancer, a particular type of cancer, gonorrhea, syphilis, an infection by a pathogen, diabetes such as diabetes mellitus, a psychiatric condition, a neurological condition, a neurodegenerative condition such as dementia, Alzheimer's, a cardiological condition, a pulmonary condition, a liver condition, a condition of the brain or another medical condition. The pathogen may include one or more of AIDS, a bacteria, a virus, a specific virus such as a coronavirus, covid-19.

In any embodiment, herein, the one or more medical conditions may also include a pre-cancerous or a premorbid condition. In regard to oncological conditions, one non-limiting example of this is a precancerous polyp or lesion. The reason that the one or more medical conditions may include a pre-cancerous or pre-morbid condition is that Applicant has discovered that specific changes in the layers (or shells) of the low disperse water envelope (LDWE) 15 and the layers (or shells) of the water mixture envelope 16, which are characteristic of a particular disease or condition, develop much earlier than the manifestation of clinical signs of the disease or condition. Therefore, certain embodiments of the water/aqua diagnostics described herein in systems 10, 200, 300, 400, method 100 are very innovative and valuable methods for early recognition of various "pre-morbid" conditions in the stage when a person feels practically healthy and has no complaints. Accordingly, these embodiments of the systems and methods allow for early diagnosis and this may be advantageous for a number of reasons, including the ability to diagnose prior to any possible (before a failure of a genome program instruction affects the physical body) and proactive correction.

As shown in FIG. 1A and FIG. 1B, the digital processing unit 40, and in particular the processor 42 by executing instructions 46, may also be configured to, for example after the spectral imaging software (or programming instructions) 45 of the processing unit 40 generates one or both of the spectrogram and image from the digitized reflected beam, determine a water fingerprint of the water mixture envelope 16. Further the digital processing unit 40, and in particular processor 42 executing instructions 46, may be configured to determine, based on the water fingerprint, and at least one of the stored reference spectra, whether the subject has one or more of the variety of medical conditions. The digital processing unit 40 may also be configured to output the determination.

For example in one embodiment, the a digital processing unit configured to store reference spectra of healthy subjects and ill subjects on a memory storage 44, and determine, after the spectral imaging software (or programming instructions) 45 of the digital processing unit 40 generates the spectrogram and/or image from the digitized reflected beam, a water fingerprint of the water mixture envelope 16, and determine, based on the water fingerprint and at least one of the stored reference spectra, whether the subject has one or more of the variety of medical conditions in one implementation by executing pattern recognition software 46 to compare a first pattern of frequencies in the water fingerprint with a second pattern of frequencies in one or more of the stored reference spectra in regard to at least one of an amplitude, phase shift, frequency shift and a chemical shift of the first and second pattern of frequencies. The digital processing unit 40 is also configured to output the determination.

Software 46 may be configured to systematize, integrate and visualize the data obtained by performing spectral analysis, Fourier transform, wavelet analysis, fractal analysis, regression analysis, cluster analysis and machine learning, special signal processing methods, representations in the form of fuzzy sets and dissipative structures. For example, the software 46 may include programs for (i) quantum-chemical calculations such as Gaussian, GAMESS, ORCA. for electron-structural calculations and analysis of energy levels, (ii) spectroscopic data processing and analysis such as SpectraSuite, Origin, MATLAB, (iii) Molecular Dynamics such as GROMACS, LAMMPS, AMBER to simulate the dynamics of molecules and hydrogen bonds and CPMD (Car-Parrinello Molecular Dynamics) for quantum-mechanical simulations of dynamics, (iv) statistical data processing and analytical software such as R, Python (with SciPy, NumPy, Pandas libraries), (v) Data Visualization such as VMD (Visual Molecular Dynamics), PyMOL to visualize molecular structures and dynamics and (vi) MATLAB, Para View for complex data visualization and analysis. Subsequently, these software tools 46 may be replaced or enhanced in some embodiments by specially created software 46 using specially trained neural networks (as well as with the ability to use quantum computers to speed up calculations.

A "signal analysis algorithm" means one or more of a Fourier transform, fast Fourier transform, a short-term Fourier transform, wavelet analysis, Hilbert transform, Haar transform and Mutifractal analysis, Spectograms, Principal Component and Independent Component Analysis algorithms, nonlinear spectral analysis, cross-correlation analysis, phase portrait and analysis of attractors, Radon conversion or machine learning algorithm.

In addition to the fast Fourier transform (FFT), the following signal analysis methods are proposed to be used in various combinations to obtain biologically significant information:

The following calculations may be useful in some embodiments of the processing by processing unit 40 including software 46: solution concentration, mass or molar concentration (expressed as the mass of the solute per volume of the solution) droplet size distribution, droplet sizes in a sprayed solution are usually described by a distribution, such as a log-normal distribution. The speed and intensity of spraying, the spray rate (where the atomization rate ν may depend on the pressure in the sprayer and the size of the opening), the spray rate (expressed as the mass or volume of the solution sprayed per unit of time), the distribution of droplets in volume (for example distribution of droplets in space can be described using stochastic models that take into account the direction and intensity of spraying, the aerodynamics of the droplets, and environmental conditions.

Droplet sizes in a cloud can be described using probability distributions. The Rosin-Rammler distribution or lognormal distribution is commonly used. Regarding surface tension and droplet size, to describe the relationship between droplet size and their physical properties, one can use Laplace's equation for capillary pressure, which is $\Delta P=\gamma(1/R\ 1+1/Rr\ 2)$, where $\Delta P$ is the capillary pressure, $\gamma$ is the surface tension coefficient, and R1 and R2 are the radii of curvature of the droplet surface. The concentration of water vapor can be described using the ideal gas equation of state, which is $PV=nRT$. To describe the dynamics of water vapor around the human body, the equation of diffusion or convection can be used.

These calculations may be performed not only for modeling, creating and describing the environment for detecting specific molecules, their concentration and distribution in the context of all other indicators and characteristics significant in the method, but also as an additional source of obtaining biologically significant information on the dynamics of the H-grid of water in the volume studied by the proposed method, including its spin component, the dynamics of the precession of the spin moment. The H-grid refers not only to the atoms (as well as ions and radicals) of hydrogen, but also to the isotopes of hydrogen, deuterium, and tritium. For this purpose, in some embodiments, gas frequency-stabilized lasers are used with a scattering and precision positioning system for the analysis of dynamic changes in the H-grid, in combination with a laser polarimeter, high-speed video cameras, mainly infrared, the interaction of which is programmatically coordinated, including with the system of preparation and spraying of specially treated water.

Although shown in FIGS. 1A and 1B as a separate component, the analog to digital converter(s) 35 of system 10 or of systems 200, 300, 400 or method 100) may also be part of the processing unit 40 or part of the at least one device 30. Alternatively, each device 30 or detector 30 may include its own analog to digital converter. In any of these implementations, the processing unit 40 is configured to receive the reflected beam (that has been digitized by an analog to digital converter 35) and, using a Fourier transform or other signal analysis algorithm (as defined herein), convert the reflected beam to a spectrogram and/or an image (the image being an image derived from the spectrogram).

References herein to "convert(ing) the reflected beam to a spectrogram and/or an image" mean converting it to a spectrogram and/or to an image derived from that spectrogram.

In any embodiment, the term "external water" refers to the water surrounding the subject's body and in particular such water after being in contact with the treated water 20. Accordingly, most precisely, the external water refers to the mixture 16 of the water envelope 15 and the treated water 20. The term "internal water" refers to the water content inside the target subject's body. The term "external water fingerprint" refer to a water fingerprint of the external water of a subject. The term "internal water fingerprint" refers to a water fingerprint of the internal water of a target subject. The term "general water fingerprint" refers to a water fingerprint of both the external water and the internal water of a target subject. The term "water fingerprint" as used in this patent application means the unique pattern of spectroscopic frequencies (or amplitudes or power or energy) for a particular target individual that is obtained from a spectrogram (generated by the digital processing unit 40) after electromagnetic radiation has been directed at the external water envelope surrounding that individual, typically after such external water envelope has been mixed with the treated water 20 to obtain a mixture 16 (the treated water thereby acting as a contrast material). The external water fingerprint may be determined by the processing unit 40 from the spectrum or spectra obtained from the external water of the target subject. The general water fingerprint may be determined by the processing unit 40 from the spectrum or spectra obtained from both the external water of the subject and the internal water of the target subject.

In any system or method described herein, laser device 32 may be adjustable both mechanically and electrically. The mechanical adjustment and/or the electrical adjustment are configured so as to select a depth of penetration of the laser beam into the water mixture envelope 16 (the mixture of the low disperse water envelope 15 (LDWE) and the treated water 20) not only in order to scan different layers of the water mixture envelope 16 but also to scan the internal body inside the target subject 12 as opposed to the external water surrounding the target subject 12.

In certain embodiments, the processing unit 40, in particular the processor 42 by executing instructions 46, is configured to obtain (i) an external water fingerprint from a spectroscopic analysis of a digital version of an electromagnetic radiation of the reflected beam of the laser device 32 and to obtain (ii) a general water fingerprint from (a spectroscopic analysis of a digital version of an electromagnetic radiation derived from) a reflected beam of the infra red device 34.

The term "external water spectrum" (or spectra) refers to the spectroscopic analysis of the digital version of the electromagnetic radiation of the reflected beam of the laser device 32. The term "internal water spectrum" (or spectra) refers to the spectroscopic analysis of the digital version of the electromagnetic radiation of the reflected beam of the infra red device 34. The term "general water spectrum" (or spectra) refers to the spectroscopic analysis of the digital version of the electromagnetic radiation of both the reflected beam of the laser device 32 and of the reflected beam of the infra red device 34. Accordingly, the general water spectra refers to the internal water spectrum and to the external water spectrum combined.

In certain embodiments, the processing unit 40 is further configured to compare each of the external water spectra and the general water spectra with the stored spectra. That is, the processing unit 40 is configured to compare the external water spectra with the stored spectra and to compare the internal water spectra with the stored spectra.

It is noted that in any embodiment the laser device 32 may be adjusted mechanically and/or electrically to focus on what it is needed to focus on. For example, laser device 32 may be adjusted so as to penetrate to a depth of the water mixture envelope 16 (of the LDWE 15 and the treated water 20) as opposed to a depth of the water inside the body of the subject 12, and likewise it may be directed to penetrate to a depth sufficient to focus on the water inside the body by a further adjustment. Furthermore, the laser device 32, as well as the infra red device 34, may be configured to direct its beam to a particular region or organ of the subject's body, such as the heart, the brain, the liver, the lungs, the legs, the abdomen, etc. This may be accomplished by adjustment of the alignment of mirrors (not shown) associated with the laser device 32. In certain embodiments, the processing unit 40 may be configured to determine that inside the subject 12 a tissue of a different texture such as a tumor is present or will be present.

Figure 8A:
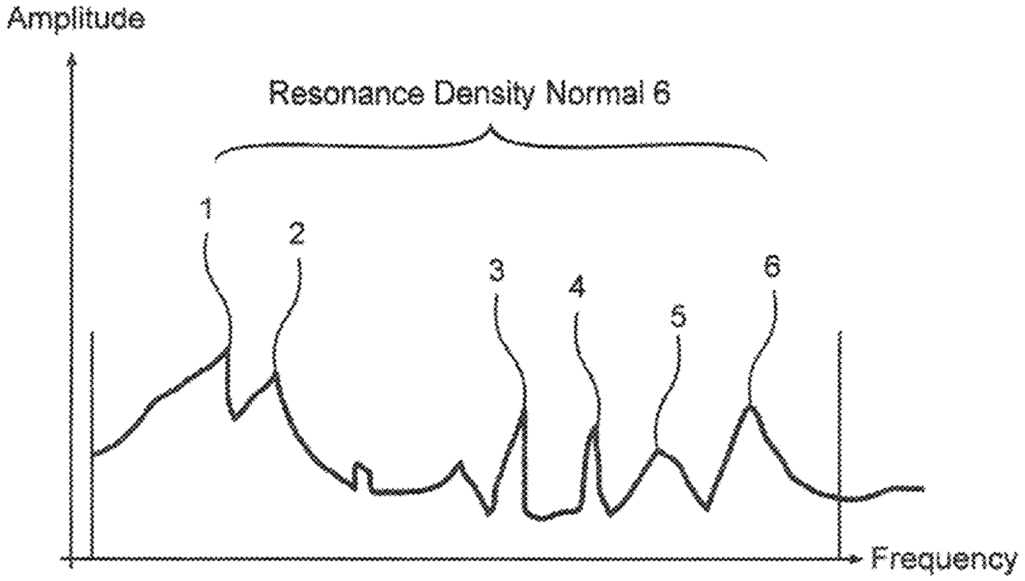
FIG. 8A shows a first graph depicting a normal resonance density for a subject, in accordance with one embodiment.
Figure 8B:
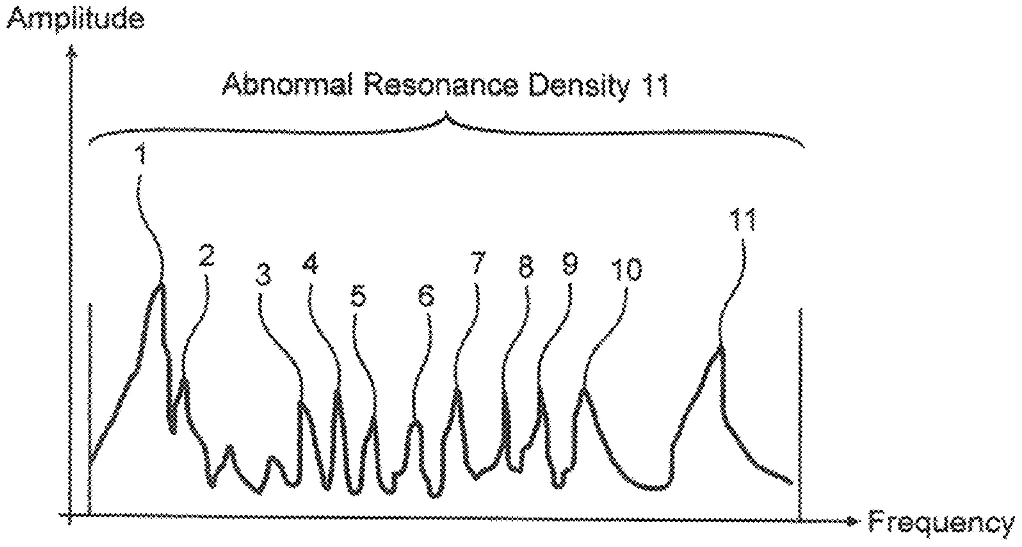
FIG. 8B shows a second graph depicting an abnormal resonance density for a subject, in accordance with one embodiment.

In some embodiments of system 10, 200, 300, 400, method 100, the determining of the water fingerprint comprises performing a spectral analysis of the external water spectra and of the general water spectra to distinguish between healthy and ill subjects based on a magnitude of a resonance density. A resonance frequency refers to a dominant frequency and also includes secondarily dominant frequencies (among the various frequencies appearing in the spectrogram), as defined herein. In this patent application, the frequency refers to the frequency of oscillation of the particles in the LDWE or in the water mixture envelope (the LDWE mixed with the treated water) that are oscillating electromagnetically. The frequency that has the highest amplitude (or power) is the dominant frequency or resonant frequency. However, if another one or more frequencies in the spectrogram are 20% or greater than 20% of the amplitude (or power) of the frequency with the highest amplitude (or power) (i.e. of the dominant frequency) then they are considered secondarily dominant frequencies. The resonance density refers to the number of different resonance frequencies (dominant frequency plus secondarily dominant frequencies) appearing (as determined by an examination of the spectrogram generated by the spectral imaging software (or programming instructions) 45 of the digital processing unit 40) in a spectrum obtained (i.e., by the spectral imaging software (or programming instructions) 45) from the electromagnetic radiation of the reflected beam. Applicant has discovered that a healthy subject has a resonance density of from 1 to about 6 (that is, between 1 and 6 different resonance frequencies). Applicant has discovered that a cancer patient, in contrast, has a resonance density of 7-14 or even higher. A finding of a resonance density of 7 or more is an indication of a pathology caused by cancer. FIG. 8A and FIG. 8B show two graphs. One graph (that of FIG. 8A) schematically depicts a normal resonance density of 6 for a particular subject. The second graph (that of FIG. 8B) schematically depicts an abnormal resonance density of 11 of a subject, which is a tentative or preliminary indication of cancer. Severe pathology caused by cancer would be indicated by a resonance density of 15 or higher. In some cases, the resonance density of an ill subject may be as high as 20 (or even a little higher).

Figure 10A:
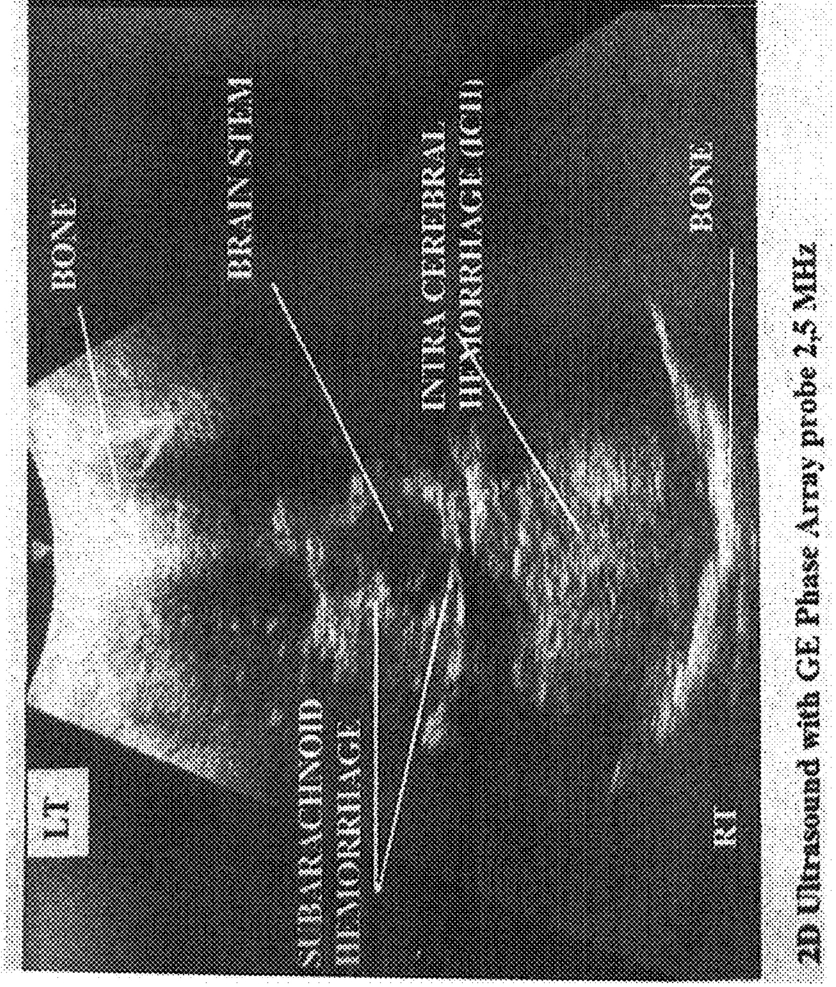
FIG. 10A shows a previous ultrasound of the subject's brain for the subject of FIG. A-FIG. H, in accordance with one embodiment.
Figure 10B:
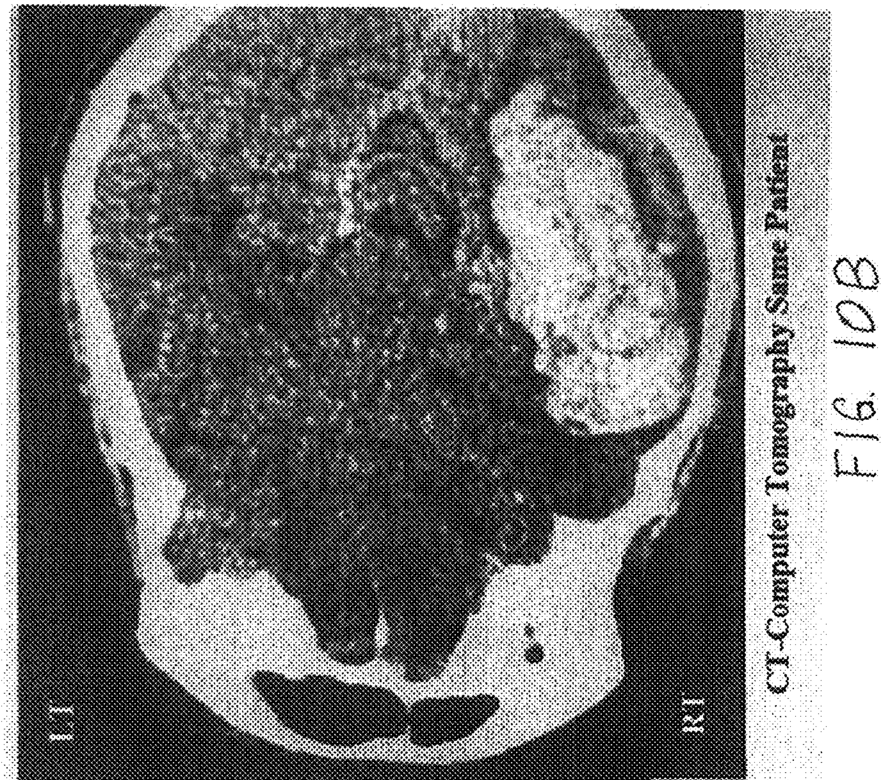
FIG. 10B shows a previous CT of the subject's brain for the subject of FIG. A-FIG. H, in accordance with one embodiment.
Figures 12A, 12B:
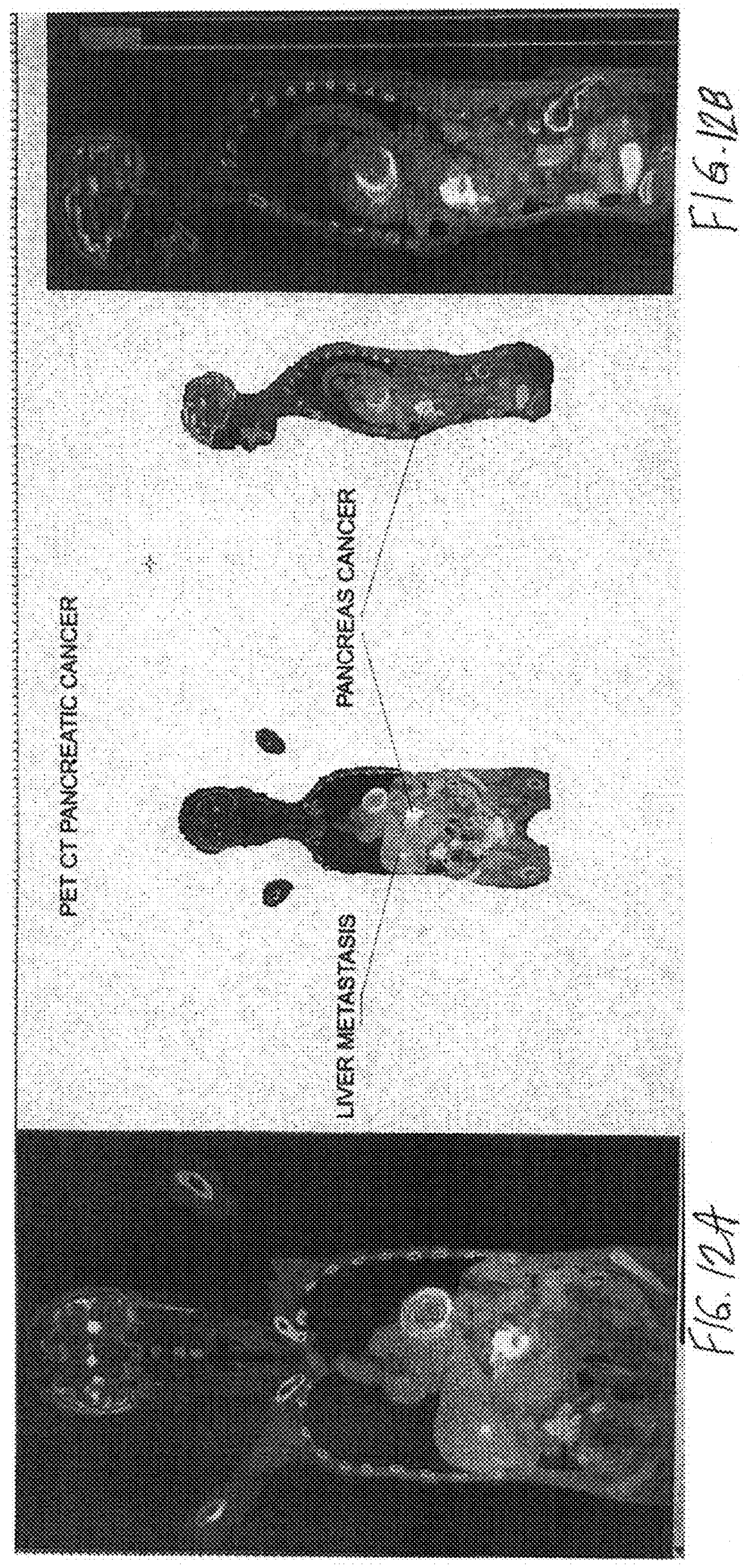
FIG. 12A is a frontal PET CT of the pancreas for the subject of FIG. 11A through FIG. 11H.
FIG. 12B is a PET CT from the side of the pancreas for the subject of FIG. 11A through FIG. 11H.

FIG. 10A shows an ultrasound of the brain of the subject of FIG. 9A-FIG. 9H while FIG. 10B shows a previous CT of this subject showing an ICH (intracranial hemorrhage).

FIG. 9A through FIG. 9H relate to human subjects that had previously undergone an ultrasound (FIG. 10A) and a CT (FIG. 10B) and been found to have a portion of an organ (in this case the brain, one hemisphere for example) that is normal and another portion of that organ that is pathological. FIG. 11A through FIG. 11H relate to human subjects that had previously undergone a frontal PET CT (FIG. 12A) and a PET CT (FIG. 12B) from the side and been found to have a portion of an organ (in this case a portion of the pancreas) that is normal and another portion of that pancreas that is pathological.

The water envelope surrounding these subjects was then sprayed with water that had been treated electrochemically by discharging the electrochemically treated water toward an area surrounding the subject (i.e. a low disperse water envelope (LDWE) for example within one meter of the subject), so as to form a water mixture envelope surrounding the subject. Then the part of the water mixture envelope adjacent (within one half a meter for example) the portion of the organ of the subject (that had been scanned by the CT or PET CT or an ultrasound) was scanned by a device 30, for example by a frequency stabilized laser device 32.

FIG. 9A and FIG. 9C show two graphs to present a comparison between a brain spectrogram (the spectrum of frequencies of the signal over time) of the water mixture envelope surrounding or adjacent the normal portion (without the brain hemorrhage) of a subject's brain (FIG. 9A) (as previously determined by a CT and an ultrasound) and a brain spectrogram of the water mixture envelope surrounding or adjacent the pathological portion of the same subject's brain in which there is an intracranial hemorrhage (ICH) (FIG. 9C) according to the previously taken CT and ultrasound.

The spectrograms of FIG. 9A and FIG. 9C were obtained by using a signal processing techniques such as Short-Time Fourier Transform, although this is not a requirement and other signal processing techniques may also be used.

FIG. 9B is a graph of the amplitude over time of the spectrogram of FIG. 9A and shows 5 peaks (a resonance density of 5) for the normal portion of the subject's brain. FIG. 9D is a graph of the amplitude of the spectrogram of FIG. 9C and shows 17 peaks (a resonance density of 17) for the portion of the subject's brain containing the ICH (as previously determined by the CT and ultrasound).

FIG. 9E through FIG. 9H are provided herein because they may be used as reference spectra to train a neural network for any method or system described herein. FIG. 9E shows a spectrogram of a normal hemisphere of a brain of the subject (of FIG. 9A) taken using a laser device 32 rather than a spectrogram of the water mixture while FIG. 9F shows a graph of the amplitude over time derived from the frequencies of the spectrogram of FIG. 9E. FIG. 9G shows a spectrogram of a pathological hemisphere of a brain of the subject (of FIG. 9C) taken using a laser while FIG. 9H shows a graph of the amplitude over time derived from the frequencies of the spectrogram of FIG. 9G.

FIG. 11A through FIG. 11D are graphs of pancreatic spectrograms, normal and pathological, for comparison, derived from scans of the water mixture envelope of the pancreas of a subject.

FIG. 11A shows a spectrogram of a water mixture envelope surrounding a normal portion of a pancreas of a subject taken using a laser, in accordance with one embodiment. FIG. 11B shows a graph of the amplitude over time derived from the frequencies of the spectrogram of FIG. 11A. It shows 7 peaks.

FIG. 11C shows a spectrogram of a pathological portion of the pancreas of the subject of FIG. 11A taken using a laser device 32. FIG. 11D shows a graph of the amplitude over time derived from the frequencies of the spectrogram of FIG. 11C, and it shows 9 peaks.

FIG. 11E through FIG. 11H are provided herein because they may be used as reference spectra to train a neural network for any method or system described herein.

FIG. 11E shows a spectrogram of a normal portion of the pancreas of the subject (of FIG. 11A) taken using a laser device 32 rather than a spectrogram of the water mixture surrounding or adjacent the pancreas while FIG. 11F shows a graph of the amplitude over time derived from the frequencies of the spectrogram of FIG. 11E and shows 5 peaks FIG. 11G shows a spectrogram of a pathological portion of the pancreas of the subject (of FIG. 11C) taken using a laser 32 rather than of the water mixture envelope surrounding the pancreas while FIG. 11H shows a graph of the amplitude over time derived from the frequencies of the spectrogram of FIG. 11G, and shows 11 peaks.

The above are examples of patients having greater numbers of peaks (i.e. greater resonance densities) in pathological portions of their body than in normal portions thereof.

By performing a spectral analysis of the external water spectra (and of the general water spectra) of the subject, the digital processing unit 40 is able to make a determination, for example an initial determination, as to whether the target subject 12 is healthy or ill based on a magnitude of a resonance density and/or based on the pattern of concentration of proteins and electrolytes in the LDWE or in the water mixture envelope.

The course of treatment of a cancer patient is expected to change the resonance density of the patient. For example, if the condition of the patient improves, the resonance density should decline toward that of a healthy person, and likewise if the condition worsens, the resonance density should increase. That is, there will be a greater number of peaks of the amplitude in the spectra of a scan taken by the system or methods described herein. There is also a unique resonance density for each type of cancer. Let us assume the resonance density of a subject who has cancer A is x and the residence density of a subject with cancer type B is y where y is x+3. If the condition of the subject with type B cancer improves—and the subject's resonance density declines sufficiently—it would be impossible to distinguish between type B cancer and type A cancer at some point solely on the basis of resonance density. Therefore, in order to distinguish between different types of cancer, taking into account the different stages of the condition after treatment, further processing may be necessary for system 10.

For example, the determining of the water fingerprint by the digital processing unit 40 in any system or method described herein may further comprise (i) subtracting the external water fingerprint from the general water fingerprint to obtain a delta signal (4) and performing a spectral analysis of the delta signal (4); and further (ii) in combination with a resonance density parameter such as the resonance density (number of different resonance frequencies), using pattern recognition software (e.g., neural network, machine learning) to perform pattern recognition of one or more of the following parameters of the delta signal: (i) an amplitude, (ii) phase shift, (iii) a frequency shift, (iv) a chemical shift.

The disclosed spectroscopic modalities, including laser-based, infrared, terahertz, and ultraviolet spectroscopy, each generate an output spectrum or spectrogram comprising a distribution of peaks or spectral features corresponding to the absorption, emission, or scattering characteristics of water vapor constituents (emitted by the subject) found in the water mixture envelope 16. The amplitude, peak locations, resonance frequencies, and phase shifts of the reflected electromagnetic signal correspond to molecular absorption characteristics that are commonly analyzed in spectroscopy to identify constituent compounds. The amplitude or intensity of each spectral peak reflects the relative concentration of the corresponding constituent. The position of each peak along the frequency or wavelength axis represents the characteristic resonance frequency of that constituent, such that frequency shifts or chemical shifts are manifested as detectable displacements of peak position. Phase information, when available from the spectroscopic modality used, is obtained from the relative phase of the detected signal and can also vary as a function of the chemical or physical environment of the vapor constituents. These spectral parameters—peak amplitude, number of peaks, peak position, frequency shift, chemical shift, and phase shift—are extracted from the acquired spectrogram and constitute the measurable features used to generate the reference patterns and to perform pattern comparison and diagnostic assessment.

In certain embodiments, the processing by the digital processing unit 40 (in any system 10, 200, 300, 400 or method 100 or another method described herein) may include determining the water fingerprint of the subject by one or more of:

(A) performing a spectral analysis of the external water spectra and the general water spectra to distinguish between healthy and ill subjects based on a magnitude of a resonance density (the magnitude of different resonance frequencies); and (B) for subjects that are ill, distinguishing between illnesses by at least one of:

(i) subtracting the external water fingerprint from the general water fingerprint to obtain a delta signal and performing a spectral analysis of the delta signal; and (ii) in combination with the resonance density parameter, using pattern recognition software to perform pattern recognition of one or more of an amplitude, a phase shift, a frequency shift, a chemical shift of the delta signal.

In general, in system 10 (or in systems 200, 300, 400 or method 100), the at least one device 30 may be configured to generate and direct one or a combination of the following six types of electromagnetic radiation: continuous laser, impulse laser, infra red, continuous terahertz, impulse terahertz, UV lower power non-ionizing radiation. Processing unit 40 may be configured using special software 46 stored on a memory 44 and executed by a digital processor 42 of the processing unit 40, such as artificial intelligence software, to integrate two or more of the six types of spectra together because each type of spectra may provide information that the other type may not. For example, using electromagnetic radiation in the UV range of 320 nm to 385 nm (and in some cases from 320 nm to 335 nm) is suitable for the determination of specific biomolecules in outer shell. In addition, electromagnetic radiation in the infra red range at for example wavelengths of 1050 to 2900 nm is absorbed quite well by water molecules compared to absorption of the visible spectrum laser radiation, and this favors imaging of the outer aqua shell (15*c*, 16*c*). Using electromagnetic radiation in the terahertz frequency range (at the frequencies described herein) has the advantage of better resolution than laser because the beam generates a smaller spot and because the scattering improves the imaging. The terahertz beam may scatter the light such that part is reflected, part is absorbed into the body of the subject, part is diffracted, and part scatters. This may facilitate building the images in a way that non-terahertz laser devices cannot do. The main laser device (if any) of system 400 (and this also true of systems 10, 200, 300, 400 and method 100), namely laser 401, may operate at wavelengths of 600 nm to 685 nm (these lasers may be helium neon frequency stabilized lasers having two modes). In addition, the infra red and near UV can provide color coded information by utilizing different codes for each layer of the LDWE 15 or water mixture envelope 16.

In embodiments in which the at least one device 30 comprises more than one device 30 and it is necessary to integrate the output from the various devices, for example but not only if there are different types of devices that direct beams of different electromagnetic radiation (or different devices that are adjusted differently so as to produce different output), software 46 may include artificial intelligence software 46, which may include machine learning instructions such as deep learning, neural networks such as multilayer neural networks, and thereby facilitate integrating the output from the different types of spectra yielded by the different types of the at least one device 30 configured to direct different wavelengths of electromagnetic radiation from different parts of the electromagnetic spectrum or by the same type of device 30 but which are adjusted differently. An example of the different adjustments of the same type of device may arise for example when using more than one laser device 30 and the devices are adjusted differently mechanically and/or the devices are adjusted electrically, thermally or piezoelectrically (or any combination thereof) in a different manner (one device compared to the other) such as by differently adjusting one or more of a frequency and a power of the laser device.

Another factor that may be used by the digital processing unit 40 of system 10 for a diagnosis or a prognosis is a presence and/or a concentration or level of an inorganic chemical element or chemical compound and/or an organic chemical compound. These elements and/or chemical compounds may be biomarkers associated with particular medical conditions. The elements or chemical compounds may include inorganic compounds or elements, such as potassium, sodium, magnesium, phosphorus, manganese, nitrogen, oxygen, carbon dioxide, hydrogen sulfide, oxygen, nitric oxide, as well as organic compounds, such as Glucose, Ammonia, Acetone, Acetylcholine, Serotonin, Cortisol, Bilirubin, Lipids, Cholinesterase, Neuropeptides, Choline, Myo-Inositol, Creatine, NAA-N Acetyl Aspartame, Neuronal Growth Factors-NGF, antibodies of a variety of diseases, various tumor markers, important enzymes, peptides and metabolites. In certain embodiments, the presence at a level of one part per billion (or another tiny amount in other embodiments) is sufficient to allow the system to detect the presence and/or concentration of the chemical element and/or chemical compound.

Each chemical compound or element has a distinctive spectroscopic pattern.

In any embodiment of system 10 or systems 200, 300, 400 or method 100, additional processing may also be performed by processing unit 40, such as Fourier transforms, fast Fourier transforms, wavelet analysis, and/or analysis of various water envelope vortices etc. Each is a separate embodiment.

In any embodiment of a system or method described herein, the output (such as a diagnosis, a tentative diagnosis, a tentative indication of, a determination of the presence of a medical condition, a determination of a chemical concentration or of a presence of a pathogen or a determination of a type of tissue or a status of a tissue or a type of cancer or a severity of a medical condition or other related information) may be presented, for example automatically, on a display screen locally or remotely. In some embodiments, some form of the output may be an audio effect perceivable by the subject, for example as an alert. For example, the initial determination of whether the subject is ill or healthy based on a diagnosis or a tentative diagnosis may be audible, or in other embodiments, is not audible.

As seen from FIG. 1B, in certain embodiments of system 200 (and this may apply also to some versions of systems 300, 400), system 200 is a non-contact rapid diagnostic system that does not include within it the treated water 20 of system 10. For example, system 200 may comprise a laser device 32 configured to direct electromagnetic radiation having a wavelength of 600 nm to 685 nm, which corresponds approximately to a frequency of 4.3765·10^8 MHz to 5.0·10^8 MHz at a target subject and/or at an area surrounding the target subject containing a low disperse water envelope (LDWE) emitted from the subject, or at an Object (such as the water content within the subject's body or the surrounding water shell/envelope of the subject)

System 200 may also comprise an infra red device 34 (not shown in FIG. 1B but shown in FIG. 2B) configured to generate and direct electromagnetic radiation having a wavelength of 1050 nm to 2900 nm, which corresponds approximately to a frequency of 1.03377·10^8 MHz to 2.855·10^8 MHz at the subject and/or at the area surrounding the subject, and may comprise a spectral imaging software (or programming instructions) 45 as part of a processing unit 40 that is configured to receive a digitized version of the reflected beam reflected from both the LDWE and water inside the subject's body and to generate a spectrogram and/or an image from the reflected beam (the digitized version being generated by the analog to digital converter 35).

System 200 may also comprise at least one device 30 that is a terahertz device 36 (not shown in FIG. 1B but shown in FIG. 2B). The terahertz device is configured to emit terahertz radiation having a frequency of 0.1 to 10.0 THz, which is from $10^5$ MHz to $10^7$ MHz (approximately 30,000 nm to approximately 3,000,000 nm). System 200 may also comprise at least one device 30 that is configured to emit near UV radiation (non-ionizing low power UV radiation) that has a wavelength of 320 nm to 385 nm, which corresponds to a frequency range of approximately $7.7868 \cdot 10^8$ MHz to approximately $9.3685 \cdot 10^8$ MHz or other versions a wavelength of 320 nm to 335 nm, which corresponds to a frequency of $8.949 \cdot 10^8$ MHz to $9.3685 \cdot 10^8$ MHz.

In one implementation, the at least one device 30 is a frequency-stabilized laser device 32 that is configured to emit non-ionizing low power UV radiation that has a wavelength of 320 nm (corresponding to $9.3685 \cdot 10^8$ MHz) (or in another implementation is configured to emit light having a wavelength of 532.8 nm (visible light)).

The UV or other electromagnetic radiation directed by the laser device 32 at the LDWE surrounding the subject impacts the particles in the LDWE. These particles, which may be particles of electrolytes or proteins, oscillate electromagnetically. These particles may be 1-60 microns in diameter. The treated water 20 that was sprayed toward the LDWE and which forms part of the water mixture envelope is configured to increase the signal to noise ratio of the reflected signal.

As with system 10 or systems 300, 400, system 200 may further comprise a digital processing unit 40 that includes digital processor 42, memory 44 on which program instructions 46 such as software 46 are stored. The program instructions 45, 46 are configured to be executed by the digital processor 42 so as to store reference spectra of healthy target subjects and ill target subjects on a memory, each of the ill target subjects suffering from one or more of a variety of medical conditions, determine, after receiving a spectrogram and/or image, a water fingerprint of the mixture of the treated water and LDWE, determine, based on the water fingerprint and at least one of the stored reference spectra, whether the target subject has one or more of the variety of medical conditions; and output the determination.

As with system 10 or systems 300, 400, in system 200 the processing unit 40 may be configured to perform any version of the processing described with respect to system 10. For example, in system 200 the digital processing unit 40 may obtain (i) an external water fingerprint from a spectroscopic analysis of a digital version of an electromagnetic radiation of the reflected beam of the laser and (ii) a general water fingerprint of both the water mixture envelope external to the subject and of water internal to the body of the subject derived from a spectrogram and/or an image generated by the spectral imaging software (or programming instructions) 45 of the processing unit 40 that received the digitized reflected beam directed by the infra red device, and to compare each of the external and general water spectra with the stored spectra. The determining of the water fingerprint comprises performing a spectral analysis of the external water spectra and of the general water spectra to distinguish between healthy and ill subjects based on a magnitude of a resonance density.

Likewise, in some implementations of system 200 or system 300 or system 400, the determining of the water fingerprint may comprise (i) subtracting the external water fingerprint from the general water fingerprint to obtain a delta signal and performing a spectral analysis of the delta signal; and (ii) in combination with a resonance density parameter, using pattern recognition software (e.g., neural network, machine learning) to perform pattern recognition of one or more of an amplitude, phase shift, frequency shift, chemical shift, of the delta signal.

In system 200, as in system 10, 300, 400, the determining of the water fingerprint may comprise one or more of:

(A) performing a spectral analysis of the external water spectra and the general water spectra to distinguish between healthy and ill subjects based on a magnitude of a resonance density; and (B) for subjects that are ill, distinguish between illnesses by at least one of:

(i) subtracting the external water fingerprint from the general water fingerprint to obtain a delta signal and performing a spectral analysis of the delta signal; and (ii) in combination with the resonance density parameter, using pattern recognition software to perform pattern recognition of one or more of an amplitude, phase shift, frequency shift, chemical shift of the delta signal.

Furthermore, the laser device 32 of system 200 (as in system 300, 400) may be any version of laser device 32 described with respect to system 10. For example, laser device 32 of system 200 may include a transmitter/receiver and may be configured to be adjusted mechanically (for example precision mechanically) the beam emitted by the laser device via an alignment of mirrors and configured to be adjusted electrically, thermally or piezoelectrically (or any combination thereof) by adjusting one or more of a frequency and a power of the laser device so as to select a depth of penetration of a laser beam into the water mixture envelope in order to scan different layers of the water mixture envelope. Laser device 32 of system 200 may be a helium-neon laser device. In system 200, the laser device 32 and the IR device 34 may be positioned 2 to 5 meters from the subject. In both system 200 and system 10, laser device 32 may include multiple laser devices and infra red device 34 may include multiple infra red devices.

It has been estimated that, roughly 60% to 80% of the human body is water, the exact percentage depending on age and other factors including the particular organ or portion of the body. According to rough estimates, for example, the liver of a human body contains about 70-75% water, the blood about 80%-90%, the kidneys about 80%-85%, the heart about 73-79%, the brain about 75%-80%, the muscles about 70%-80% and the bones about 22%-31% water. With illness, the first chemical substance to change is the water. Water concentration is highly regulated in the healthy human brain and changes only slightly with age in healthy subjects. Consequently, changes in water content are important for the characterization of disease. Magnetic resonance imaging (MRI) can be used to measure changes in brain water content. However, since these changes are usually in the low percentage range, highly accurate and precise methods are required for detection.

With regard to water content in the brain of a subject, embodiments of the invention described herein (in any system 10, 200, 300, 400 or method 100 or another method described herein) may be used for diagnosis and visualization of water content in the brain in a manner that is superior to the MRI. For one thing, in certain embodiments herein, the speed of the determination of the digital processing unit 40 may be less than five seconds, less than one second, less than 0.5 seconds or less than 100 milliseconds. Each option is a different embodiment. Obviously, an MRI result typically takes days or even longer. In addition, certain embodiments described herein do not require the active participation of the subject and do not require contact with the subject or the provision of a sample by the subject, in contrast to an MRI which requires having the target subject lie down in a very uncomfortable position for half an hour or an hour or longer. Furthermore, unlike an MRI, which cannot detect the presence of the water envelope surrounding the target subject, or the water mixture envelope 16 surrounding the target subject and the treated water 20, certain embodiments described herein are able to detect and monitor the content of the low disperse water mixture envelope 16 surrounding the target subject's body that has been affected by the treated water 20. This is so even though this water mixture envelope 16 may be invisible to the naked eye. Furthermore, in some embodiments, the system 10 (or systems 200, 300, 400) and/or method 100 is able to monitor not only the content of the water in the body of the target subject and outside the body of the subject so as to form a diagnosis of a medical condition or a functional condition (or in other embodiments at least a critical tool used in the repertoire needed for the diagnosis), but also allows a determination of a concentration of important chemical elements or compounds in the body of the target subject and in the water mixture envelope 16 surrounding the target subject 12. This includes both inorganic compounds or elements, such as potassium, sodium, magnesium, phosphorus, manganese, nitrogen, oxygen, carbon dioxide, hydrogen sulfide, oxygen, nitric oxide, as well as organic compounds, such as Glucose, Ammonia, Acetone, Acetylcholine, Serotonin, Cortisol, Bilirubin, Lipids, Cholinesterase, Neuropeptides, Choline, Myo-Inositol, Creatine, NAA-N Acetyl Aspartame, Neuronal Growth Factors-NGF, antibodies of a variety of diseases, various tumor markers, important enzymes, peptides and metabolites.

In determining the presence of a chemical compound or chemical element, certain embodiments of system 10, 200, 300, 400 and method 100 achieve a remarkable level of precision with respect to identifying whether the chemical substance is present. For example, it is configured to be sensitive enough to detect even one molecule per billion of glucose or another compound of chemical element.

Furthermore, certain embodiments are superior to a positron emission tomography (PET) scan or a CT scan, which relies on positrons or dye material or other material for contrast material. Instead, certain embodiments herein rely on the treated water 20, such as electrocoagulated water 20, to function as a contrast material, thereby rendering positrons unnecessary. The treated water 20 may be merely sprayed toward the invisible water envelope surrounding the subject without the subject having to take an action, and in some cases without the target subject feeling the treated water 20. In some embodiments, at most, the target subject 12 may feel a region of higher humidity briefly.

In certain embodiments, system 10, system 200, system 300, system 400 or method 100 may also be configured to track-without contact with the target subject, the subject's pH and acidity, or the acidity or pH of particular organs or locales of the target subject's body.

In any of the systems described herein (for example 10, 200, 300, 400) the low disperse water envelope (LDWE) 15 emitted by the subject is not part of the system.

Figure 7:
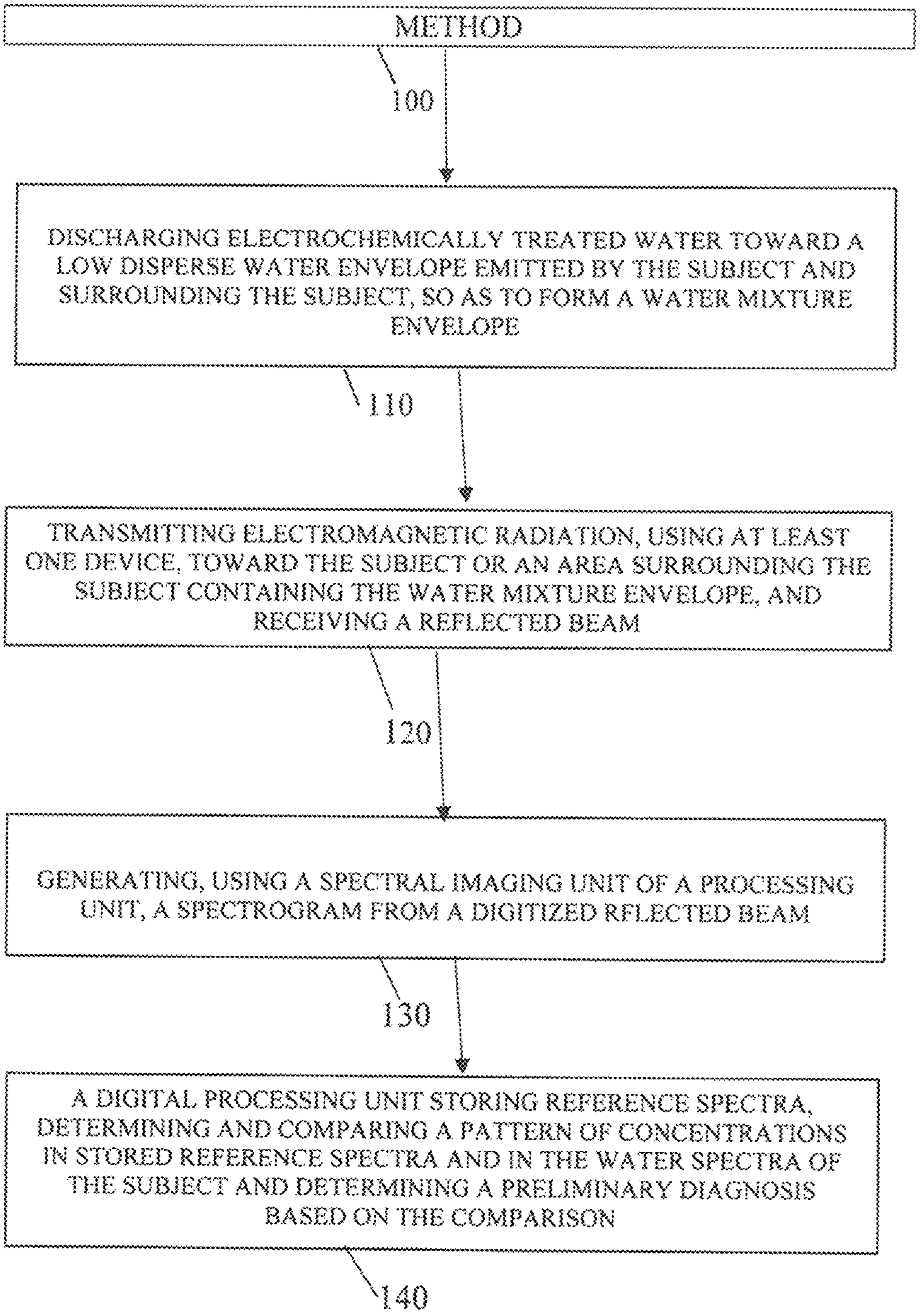
FIG. 7 is a flow chart showing a method, in accordance with one embodiment.

As seen in FIG. 7, another embodiment is a method 100 of non-contact rapid diagnosis of a target subject, for example a method 100 that utilizes a water Object associated with the target subject without active participation of the target subject. Method 100 may include a step 110 of discharging treated water 20, such as electrochemically treated water such as electrocoagulated water 20, toward a low disperse water envelope 15 (LDWE) that has been emitted by (or is being emitted by) the target subject (which LDWE envelope is understood to include molecules of the products of the vital activity of the water emitted by the target subject), the LDWE surrounding the subject, so as to form a low disperse water mixture envelope 16. The scanned volume around the subject can be said to reflect the functional state of the Object (i.e., the water within and surrounding the subject). In the low disperse water mixture envelope 16, the treated water 20 may advantageously function as a contrast material.

The emitting of the low disperse water envelope 15 (LDWE) by the subject is not a step of method 100. Rather it is a condition that the subject's body creates continually. The subject's body normally constantly emits this low disperse water around the subject transdermally, through the target subject's nose and/or mouth (or other apertures as described) so as to create this LDWE 15.

The treated water 20 that is discharged in step 110 may be in a form of a spray or a mist when it is discharged. The discharging of the treated water 20 may involve discharging the water by spraying the water from an apparatus that initially contains the electrochemically treated water 20 and then discharges the treated water 20 in the form of a mist or spray. In some embodiments, the treated water once sprayed or once put into a mist form has particles ranging in diameter from 20 to 50 microns.

Step 110 may also include the process of treating the water. Such water treatment may include pre-treatment and/or reverse osmosis and/or bidistillation followed by electrocoagulation with various electrodes (soluble and insoluble), and one or more of electroflotation, separation and discharge of the coagulant, subsequent cleaning from residues of coagulant, and in some cases mixing with chemical reagent indicators.

In method 100 the treated water may be any version or subversion of the water 20 described herein with respect to any system (for example system 10 or system 200 or system 300 or system 400 or any other system described herein). For example, the treated water 20 may be treated by an electrochemical process as described in regard to any of the systems described herein, the LDWE and the water mixture envelope may comprise particles of 1-60 microns in diameter, the treated water 20 may vary with respect to an ORP of −70 mV to −150 mV or a pH or 4.5-9 (or 4.5-10). In order to maximize the effectiveness of the treated water 20 as a contrast material, step 110 of method 100 may be implemented by discharging electrochemically treated water that has been preparing utilizing an electrochemical process that utilizes an oxidative reduction potential (ORP) that is as close as possible to the range of −70 mV to −150 mV.

For example, in some embodiments of method 100 (or system 10, 200, 300, 400) the treated water 20 is prepared through an electrochemical process such as electrocoagulation that utilizes an amount of ORP that varies within the range of 0 to −200 mV or −50 mV to −200 mV, or −150 mV to 0 mV or 0 mV to −250 mV, or 0 mV to −300 mV or 0 mV to −400 mV, or from −200 mV to 0 mV or 0 to −100 mV. Each range is a separate embodiment (or alternatively in any range described with respect to system 10 or system 200). Furthermore, the water may be supplied in accordance with a special program in an adjustable pulse mode in which the supply pressure is regulated.

Some embodiments of method 100 may include a step of starting, testing and calibrating the system, including scanning calibration samples in static and/or dynamic modes, and space marking for the scanning.

Method 100 may also comprise a step 120 of transmitting electromagnetic radiation, using at least one device (32, 34), toward the subject 12 or an area surrounding the subject containing the water mixture envelope 16, and receiving a reflected beam, for example by an analog to digital converter that digitizes the reflected beam and transmits the digitized reflected beam to the digital processing unit 40 that includes spectral imaging programming instructions 45.

In certain embodiments, method step 120 may include controlling the transmission of the electromagnetic radiation using the processing unit including software and wherein the at least device may be at least one frequency stabilized laser guided (to a scanned volume surrounding the subject) to the active adjustable mirror(s), by partially passing the laser beam through the splitter 405 to the polarimeter and photodetector 406, 418 (CCD array), so as to completely or partially scan the scanned volume, while matching corresponding values of deflection angles of the adjusted mirror(s) 403, 404, 415, 434 and the distance from the active mirror. In some cases, the at least one laser in infrared range or in terahertz range includes mirrors, dividers, expanders, CCD matrices, at least one laser in terahertz range. Additionally, in certain embodiments method 120 also utilizes a set of EMP sources (coherent and incoherent, pulsed and constant) for greater contrast.

Some versions of method 100 also include a step of converting the data received from each analog source (for example a laser device 30 or a camera or other analog detector) in analog form to digital form, for example using an analog to digital converter.

Method 100 may include step 130 of generating, using the spectral imaging software (or programming instructions) 45 of a digital processing unit 45, a spectrogram from the reflected beam and/or an image derived from the spectrogram.

Step 140 of method 100 may comprise executing instructions, by a digital processing unit 40, to perform: storing reference spectra (derived from PET CT, CT or MRI or the frequency-stabilized laser scanning of the organs or body parts such as the brain or pancreas) of healthy subjects and ill subjects on a memory, each of the ill subjects suffering from one or more of a variety of medical conditions (such as cancer of the pancreas or brain hemorrhage); finding a first pattern of frequencies in the stored reference spectra (for example based on one or more of an amplitude, phase shift, frequency shift and a chemical shift of frequencies in the reference spectra) and deriving a first pattern of concentrations of electrolytes and protein molecules in the stored spectra, determining, using the spectrogram and/or image, a second pattern of frequencies in a water spectra of the subject based on the one or more of the amplitude, phase shift, frequency shift and a chemical shift of frequencies in the water spectra of the subject and derive a second pattern of concentrations of electrolytes and protein molecules in the water envelope mixture of the subject from the second pattern of frequencies using the neural network; comparing the first and second patterns of concentrations and determining, based on the comparison whether the subject has one or more of the variety of medical conditions; and optionally outputting the determination.

In method 100 any version of the devices or equipment described with respect to any system 10, 200, 300, 400 is also applicable to such device or equipment mentioned in method 100. In method 100, the at least one device 30 may comprise a laser device 32 and method 100 may further comprise using the electrocoagulated water as a contrast material vis a vis the LDWE in processing the spectrogram and/or image derived from the reflected beam reflected from the laser device 32.

The at least one device 30 of method 100 (or any equivalent device described herein such as device 301, 401 configured to direct electromagnetic radiation at a target subject or at an area surrounding the subject or at an Object such as water content within or surrounding the body of the target subject) in any system 200, 300, 400) may comprise a laser device 32. Method may include transmitting, using the laser device, electromagnetic radiation having a wavelength of 600 nm to 685 nm, which corresponds approximately to a frequency of 4.3765·10^8 MHz to 5.0·10^8 MHz. Method 100 may include using a laser device that is a frequency-stabilized laser device, such as any version described with respect to system 10.

In some versions of method 100, the at least one device 30 may comprise or may also comprise one or more infra red devices 34. For example, the electromagnetic radiation emitted by the infra red device may have a wavelength of 1050 nm to 2900 nm, which corresponds approximately to a frequency of 1.03377·10^8 MHz to 2.855·10^8 MHz. In some versions of method 100 the at least one device 30 may comprise or may also comprise a terahertz device 36 that emits terahertz radiation having a frequency of 0.1 to 10.0 THz, which is from 10^5 MHz to 10^7 MHz (approximately 30,000 nm to approximately 3,000,000 nm). In some versions of method 100, the at least one device 30 may comprise or may also comprise a device 30 that emits or transmits near UV radiation (non-ionizing low power UV radiation) that has a wavelength of 320 nm to 385 nm, which corresponds to a frequency range of approximately 7.7868·10^8 MHz to approximately 9.3685·10^8 MHz or other versions a wavelength of 320 nm to 335 nm, which corresponds to a frequency of 8.949·10^8 MHz to 9.3685·10^8 MHz.

The at least one device 30 may comprise a laser device 32 and method 100 may further comprise adjusting the beam emitted by the laser device mechanically (for example precision mechanically) via an alignment of mirrors and adjusting the laser device electrically, thermally or piezoelectrically (or any combination thereof) by adjusting one or more of a frequency and a power of the laser device so as to select a depth of penetration of a laser beam into the water mixture envelope in order to scan different layers of the water mixture envelope.

Step 140 of method 100 may further comprise using the digital processing unit 40 to determine (i) an external water fingerprint from a spectroscopic analysis of a spectrogram and/or image generated by a spectral imaging software (or programming instructions) 45 (of the digital processing unit 40) derived from the reflected beam of the electromagnetic radiation emitted by the laser device and (ii) a general water fingerprint of both the water mixture envelope external to the target subject and of water internal to the body of the target subject derived from the spectrogram and/or image generated by the spectral imaging software (or programming instructions) (that converted the digitized reflected beam directed by the infra red device), and comparing each of the external and general water spectra with the stored spectra. In that case, the at least one device comprises a laser device 32 and an infra red device 34.

In some embodiments, step 140 of method 100 may comprise determining of the water fingerprint by performing a spectral analysis of the external water spectra and of the general water spectra to distinguish between healthy and ill subjects based on a magnitude of a resonance density.

In certain embodiments, step 140 of method 100 may comprise determining the water fingerprint by:

(i) subtracting the external water fingerprint from the general water fingerprint to obtain a delta signal and performing a spectral analysis of the delta signal; and (ii) in combination with a resonance density parameter, using pattern recognition software to perform pattern recognition of one or more of an amplitude, phase shift, frequency shift, chemical shift of the delta signal.

In some embodiments, step 140 of method 100 may comprise determining the water fingerprint by one or more of:

(A) performing a spectral analysis of the external water spectra and the general water spectra to distinguish between healthy and ill subjects based on a magnitude of a resonance density; and (B) for subjects that are ill, distinguish between illnesses by at least one of:

(i) subtracting the external water fingerprint from the general water fingerprint to obtain a delta signal and performing a spectral analysis of the delta signal; and (ii) in combination with the resonance density parameter, using pattern recognition software to perform pattern recognition of one or more of an amplitude, phase shift, frequency shift, chemical shift of the delta signal.

The variety of medical conditions mentioned with respect to system 10 or systems 300, 400 apply equally to system 200 and to method 100.

Method 100 may also have a step of using the outputted water fingerprint for artificial intelligence training, for example by training a supervised dataset or an unsupervised dataset, and replenishing the standards.

FIG. 2A includes a non-limiting example of a system 300 and an associated block diagram showing certain optional elements of that system 300 as part of a workflow. System 300 may include optional detectors 301 (sensors) of spectrometers, photopolarimeters, or detectors (sensors) of humidity, UV, IR and THz, ultrasound. System 300 may include optional humidifiers 302 and frequency stabilized lasers 32 (in any version of the frequency stabilization described herein including those described with respect to systems 10, 200).

System 300 may also include a detection circuit frame 304 that may have detectors projecting therefrom and optionally transparent floor with ultrasonic and IR scanners 34, video cameras 305, camcorders 305 including optionally stereo camcorders 305 or high speed camcorders 305 (from 25 to 10,000 fps) and other detectors.

System 300 may include optional element 306, namely infrared traces, which are dynamic tracers of the residual heat radiation of the person (or animals) and acoustic traces, which embody or reflect the manner of movements and sounds uniquely characteristic of this person.

In FIG. 2A, one can see the volume 307 surrounding the subject 12 containing the low disperse water envelope 15 and the treated water 20 to form the mixture 16. This area can be considered the scanned volume around the subject 12.

As seen in FIG. 2A, the data from all of the possible detectors or sensors is transmitted to a data acquisition unit 308 comprising digital to analog converters that are configured to receive the data from the optional detectors, high-speed video cameras and the quantum dots representing the water particles in the water mixture envelope 16, and to transmit the digital data to the processing unit 313.

System 300 may include the elements of either system 10 or system 200 (such as at least one device 32) and may also comprise an electrochemical unit 309 configured to produce/provide special water treatment 20 such as by electrochemical treatment such as electrocoagulation. Unit 309 may also include a container or chamber for storing water prior to such treatment.

FIG. 2A shows that system 300 may also comprise a water spray (humidification) control system 310 in certain embodiments that may be configured to spray specially prepared/treated water 20 (in sprayed or atomized or mist form) toward the low disperse water envelope 15 surrounding the target subject or each target subject 12.

Block 313 shows a processing unit 313 that may be any version of the previously described processing unit 40 and may include program instructions 46 stored on memory 44. Analysis of the received data may also optionally use an AI system. Block 312 shows a database 312 of reference spectra stored on memory 44 of processing unit 313.

Block 314 shows an optional input/output unit 314, block 315 shows an optional unit 315 of control and management and block 316 depicts an optional energy supply system 316.

Figure 3:
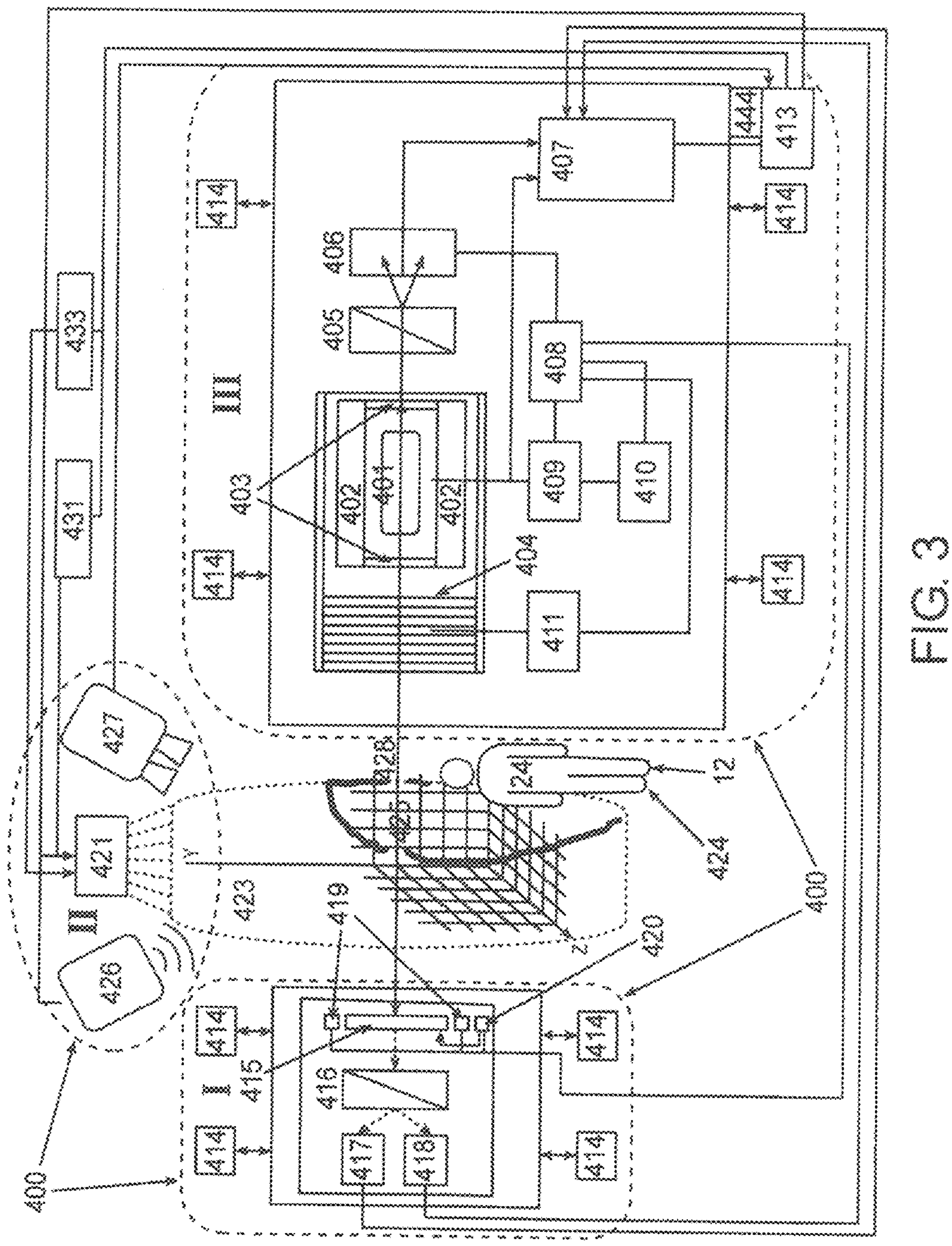
FIG. 3 is a schematic illustration of a system, in accordance with one embodiment.

FIG. 3 depicts one non-limiting version of a system 400 for non-contact rapid diagnosis. It should be understood that system 400 need not contain all or even most of the components that appear in FIG. 3. The components depicted in FIG. 3 and FIG. 4 and listed below are optional except that system 400 does include at least one device 401 and does include a processing unit 413. The at least one device 401 of system 400 may include at least one of a laser device, an intra red device a terahertz device and a device that emits UV non-ionizing electromagnetic radiation (as in the at least one device 30 of systems 10, 200, 300 and method 100 such as devices 32, 34, 36, 37) for directing electromagnetic radiation at the target subject or the area surrounding the target subject The water within the target subject and the area surrounding the target subject may also be called an "Object" or a "water Object" since it is the water content (i.e., Object) that is either within or surrounding the body of the target subject that is targeted, in accordance with certain embodiments herein.

System 400 includes one or more of the components in one or more of the following groups of components: (a) "Group I", which includes components for positioning and pairing an active mirror for the correct partial reflection of the scanning laser beam back into the active element of the laser with a photodetector and a polarimeter, (b) "Group II", which includes components for positioning and directing sprayed specially prepared water 20 with sources of radiation (coherent and incoherent) for highlighting the scanned volume with a scanning (interacting) laser radiation and high-speed stereo cameras, and (c) "Group III", which includes components for positioning and interfacing with an active mirror of scanning laser radiation with the necessary characteristics with a frequency stabilization system, a data acquisition unit, analog-to-digital converters.

As shown in FIG. 3 (and in some cases in FIG. 4), system 400 may include one or more of the following components:

System 400 may comprise a working body of a laser 401, such as a frequency-stabilized laser device 401, configured to direct electromagnetic radiation at the target subject or Object or area surrounding the target subject. Laser device 401 may also be in any of the versions described for the laser device 32 of systems 10, 200, 300 (and method 100) including any version of the frequency stabilization described with respect to any of these systems or method 100. System 400 may also comprise one or more thermal and piezo drives 402, controllers 409 for controlling the one or more thermal or piezo drives 402 and a power supply 410 that supplies power to the controllers 409. System 400 may also include a frequency stabilization control system 408 for stabilizing the frequency of the laser device 401.

System 400 may also include one or more mirrors 403 for mechanical adjustment of the beam of the laser device 401. The system 400 may also include other components for mechanical adjustment of laser device 401 such as one or more focusing lenses 404, expanders 404, mirrors 404, Fresnel diamond lenses 404, zero order lenses 404 and filters 404, as well as controllers 411 and drives 411 for controlling the mirrors 404, filters 404, lenses 404 and expanders 404.

The laser device 401 may also include other components such as one or more dividers 405 and polarization splitters 405.

System 400 may also include one or more photodetectors 406 (as an option, a phased array of photodetectors of multifractal dimension) to measure the output of the laser 401.

System 400 may further comprise one or more analog to digital converters 407 that receives the data or output from the at least one device—for example from laser 401—(i.e. the at least one device that is configured to (i) direct electromagnetic radiation at a subject and/or at an area surrounding the subject containing a water mixture envelope 16 (for example comprising a mist or sprayed form of the treated water and a low disperse water envelope (LDWE) emitted from the subject's body) or any other detector).

System 400 also include a processing unit 413 that may include a processor 42 and associated hardware and programmable instructions or software 46 for visualization of the functional state of a person's aqua hologram (or the Object, for example water, being targeted). The processing unit 413 also encompasses any version of a processing unit described with regard to processing unit 40. Analog-to-digital converters 407 may be positioned physically or operatively between processing unit 413 and polarimeter and photodetector 406.

As seen in FIG. 3, system 400, for example subsystem III, may include processing unit 413 that may also comprise spectral imaging software (or programming instructions) 444 that is part of (and stored on the memory of) the processing unit 413. The digital processing unit 413 is configured to receive a digital version of the reflected beam and convert the digitized reflected beam to a spectrogram and/or an image, for example using a Fourier transform or other signal analysis algorithm. Subsystem 414 of system 400 ("I") may be a stationary system of mutual conjugation and three-dimensional spatial mutual positioning, taking into account the main needs of the frequency stabilization control system 408 (in "III").

Subsystem 414 may comprise mirrors 415 (which are used to reflect the required amount of scanning beam of a frequency-stabilized laser back into the emitter) or mirror-related components configured to adjust a beam by the parameter of the percentage of reflection and the angle of the plane of inclination mirror. Subsystem 414 may also include a divider, a polarimeter 417. Subsystem 414 may further include one or more photodetectors 418, stepper motors 419 and piezo drives 419 for precision mirror positioning and a controller 420 for regulating the percentage of transmission (reflection) of the laser beam.

As can be seen from FIG. 3, system 400 may include a special water treatment unit 431 configured for providing any version of treated water 20 described herein (for example in sprayed or mist or atomized form). In some embodiments, system 400 also includes the treated water 20 itself. System 400 may also include a mechanism 421 or container 421 or device such as one or more dispensers, mixers and sprayers configured to hold and/or mix and then spray or otherwise dispense finely dispersed specially prepared water 20 at a volume 423 surrounding a target subject 12. In some cases, system 400 is configured to add certain special chemical or other reagents before spraying or otherwise discharging treated water 20.

In FIG. 3, the scanned Object 424 comprises both the "internal" water content of the target subject and the outer aqua shell of a target person 12. The inner aqua shell of a person 12 is all the water within the boundaries of (i.e., internal to) the skin of the human body, as well as within the skin itself. The outer water (aqua) shell of a target person is water in a liquid and/or gaseous state, released by the skin, lungs, etc., and surrounding the person. It is divided into three layers 16*a*, 16*b*, 16*c* (FIG. 6*b*): an innermost layer called "fountain" which is from the skin surface to 20 mm outward, a middle layer called "vortex" which is from 20 mm from the skin outward to 700 mm from the skin (2 cm to 70 cm from the skin) and an external layer from 700 mm (0.7 meter) from the skin up to 500 mm (0.5 meter) from the skin or in other embodiments up to 1000 mm (1 meter) or in certain embodiments even beyond that.

Component 425 is the scanned volume 425, which means a part of the space around a person, for example up to 1 meter in all directions from the skin surface, in which the physical fields generated by a person, as well as external physical fields modulated by his body, interact with specially treated or prepared sprayed water 20 or water mist. The specified volume 425 is scanned by the system 400 shown in FIG. 3. Emitters 426 are optional components for "illuminating" the scanned volume (coherent and incoherent). System 400 may also include in certain embodiments high-speed stereo cameras 427 with filters (including in the IR and UV ranges), receivers of electromagnetic radiation in a wide range and magnetic field detectors.

FIG. 4 depicts a generalized version of FIG. 3 using movable chambers/containers 430 such as drones to house various components of the system 400. The drones shown in FIG. 4 may also be used to house any of the components or groups of components in systems 10, 200, 300.

Component 428 (FIG. 3, 4) represents the scanning (interacting) laser radiation. Component 433 (FIG. 3) is an optional unit for preparation of chemical reagents.

In the generalized version with drones 430, system 400 may also include a mobile system 429 of spatial positioning configured to pair drones 430 with respect to the scanned Object or target person 12, taking into account the main needs of the frequency stabilization system 408.

As shown in FIG. 4, a group of stationary or movable inanimate bodies or objects 430 may house portions of system 400. In the case of movable inanimate bodies or objects, these movable inanimate bodies or objects may be drones 430. As shown further in FIG. 4, system 400 may include a base station 432 for launching or holding movable container/chambers 430 such as drones 430, including a device for recharging, testing, special water treatment and refueling, devices for preparing chemical reagents (indicators) and refilling them into a drone.

Figure 5:
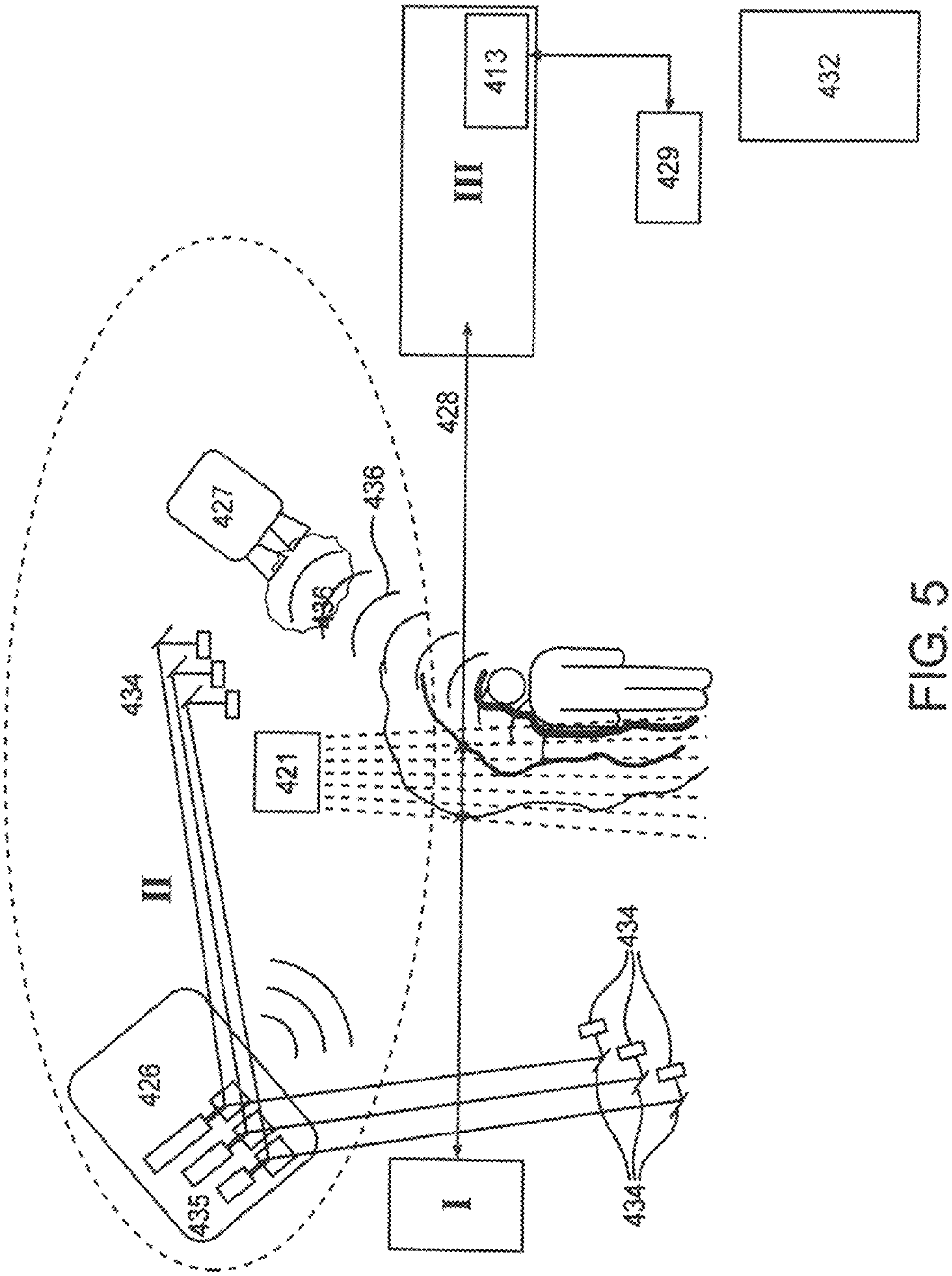
FIG. 5 is a schematic illustration of portions of the system of FIG. 3 including a laser module, in accordance with one embodiment.

FIG. 5 shows further details of a particular implementation of system 400. A component of subsystem II in FIG. 5, called a laser module 435, may include at least one device (such as the devices 32, 34, 36, 37 of system 10 shown in FIG. 2B) such as a laser with radiation in the ultraviolet range, a laser with radiation in the infrared range, a laser with radiation in the terahertz range with dividers (or alternatively one or more of a combination of the three). The radiation directed from the laser module 435 may be transmitted to a system of controlled mirrors 434 that may include expanders or optical fiber with expanders. Cameras 427 or another recording medium may record reflected non-ionizing electromagnetic radiation 436 whose wavelength is in what is referred to as the primary multi-range (the infrared range, the terahertz range and the ultraviolet range). Such non-ionizing electromagnetic radiation may also be displayed in the recording medium, for example cameras 427.

As shown in FIG. 5, system 400 may further comprise at least one of: (i) a terahertz device (for example device 36) and the electromagnetic radiation that is emitted by the terahertz device has a frequency of 1.0·10ˆ5 MHz to 1.0·10ˆ7 MHz (which corresponds to a range of wavelengths of approximately 30,000 nm to approximately 3,000,000 nm), and (ii) a device configured to emit non-ionizing UV radiation (for example device 37) that has a wavelength of 320 nm to 385 nm which corresponds to a frequency of 7.7868·10ˆ8 MHz to 9.3685·10ˆ8 MHz (and in some cases has a wavelength of 320 nm to 335 nm) and controlled mirrors 434 with expanders 434 or optical fiber with expanders. Mirrors 434 may be used to construct a hologram in various spectra from ultraviolet to terahertz.

One embodiment is a non-contact rapid diagnostic system configured to analyze a water Object of a target subject, the water Object accessible to the system without active participation of the target subject, the system comprising:

at least one device 30 configured to direct electromagnetic radiation at the subject and/or at an area surrounding the subject containing a water mixture envelope comprising a mist or sprayed form of the treated water and a low disperse water envelope (LDWE) emitted from the subject's body, wherein in some implementations of this embodiment the electromagnetic radiation has at least one of the following wavelengths: (i) 320 nm to 385 nm, (ii) 600 nm to 685 nm, (iii) 1050 nm to 2900 nm;

an analog digital converter configured to receive and convert the reflected beam to a digitized reflected beam, a digital processing unit 40 configured to:

receive and convert a digitized reflected beam into a spectrogram, or a spectrum and an image derived from the spectrogram, using a signal analysis algorithm such as a Fourier transform;

store reference spectra of healthy subjects and ill subjects on a memory, each of the ill subjects suffering from one or more of a variety of medical conditions;

determine, after generating the spectrogram and/or the image, a water fingerprint of the water mixture envelope;

determine, based on the water fingerprint and at least one of the stored reference spectra, whether the subject has one or more of the variety of medical conditions; and output the determination.

This embodiment encompasses any version of the at least one device 30 described herein and any version of the digital processing unit 40 described herein including any version of the spectral imaging software (or programming instructions) 45 described herein and any version of the description of the water mixture envelope described and any version of the electrochemically treated water 20 described herein. Each version is a separate embodiment.

One embodiment is a method of non-contact rapid diagnosis of a subject, the method making use of a water Object associated with the subject, without active participation of the subject, the method comprising:

transmitting electromagnetic radiation, using at least one device, toward the subject or an area surrounding the subject and containing a water mixture envelope formed as a mixture of: (a) a low disperse water envelope (LDWE) emitted by the subject, the LDWE surrounding the subject so as to be within 5 meters of the subject and (b) electrochemically treated water discharged toward the LDWE;

using an analog to digital converter to convert the reflected beam into a digitized reflected beam;

executing instructions, by a digital processing unit, to perform:

using a signal analysis algorithm such as a Fourier transform, convert the digitized reflected beam into a spectrogram or also an image derived from the spectrogram, storing reference spectra of healthy subjects and ill subjects on a non-transitory computer readable storage medium, each of the ill subjects suffering from one or more of a variety of medical conditions, the variety of medical conditions comprise cancer, diabetes, a sexually transmitted disease and diseases caused by pathogens in the subject's body;

determining, using the spectrogram and/or image, a water fingerprint of the water mixture envelope;

determining, based on the water fingerprint and at least one of the stored reference spectra, whether the subject has one or more of the variety of medical conditions by executing pattern recognition software to compare a first pattern of frequencies in the water fingerprint with a second pattern of frequencies in one or more of the stored reference spectra in regard to at least one of an amplitude, phase shift, frequency shift and a chemical shift of the first and second pattern of frequencies; and outputting the determination.

This method encompasses any version of the at least one device 30 described herein and any version of the digital processing unit 40 described herein including any version of the spectral imaging software (or programming instructions) 45 described herein and any version of the description of the water mixture envelope described and any version of the electrochemically treated water 20 described herein. Each version is a separate embodiment.

Another embodiment is a non-contact rapid diagnostic system configured to analyze a water Object of a target subject, the water Object accessible to the system without active participation of the target subject, the system comprising:

a laser device configured to (i) direct electromagnetic radiation having a wavelength of 600 nm to 685 nm at the subject and/or at an area surrounding the subject containing a low disperse water envelope (LDWE) emitted from the subject mixed with treated water 20 to form a water mixture envelope;

an infra red device configured to (i) direct electromagnetic radiation having a wavelength of 1050 nm to 2900 nm at the subject and/or at the area surrounding the subject (containing the LDWE mixed with treated water 20 to form the water mixture envelope);

an analog to digital converter configured to receive the reflected beam reflected from both the water mixture envelope and water inside the subject's body and convert it to a digited reflected beam;

a digital processing unit configured to:

use a Fourier transform or another signal analysis algorithm to generate a spectrogram (or also an image derived from the spectrogram) from the digitized reflected beam, store reference spectra of healthy subjects and ill subjects on a memory, each of the ill subjects suffering from one or more of a variety of medical conditions;

determine, after receiving a spectrogram and/or an image, a water fingerprint of the water mixture envelope (the mixture of the treated water and the LDWE);

determine, based on the water fingerprint and at least one of the stored reference spectra, whether the subject has one or more of the variety of medical conditions; and output the determination.

In any system or method (including systems 10, 200, 300, 400 or method 100 or another method) described herein the computer-accessible storage medium 44 may include any tangible or non-transitory storage media or memory such as electronic, magnetic, or optical media coupled to computer processing unit 40 (for example via bus) including flash memory. The terms "tangible" and "nontransitory," as used herein, are intended to describe a computer-readable storage medium (or "memory") excluding propagating electromagnetic signals but are not intended to otherwise limit the type of physical computer-readable storage device that is encompassed by the phrase computer-readable medium or memory. For instance, the terms "non-transitory computer readable medium" or "tangible memory" are intended to encompass types of storage devices that do not necessarily store information permanently, including for example, random access memory (RAM). Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

In some other embodiments of any of the systems or methods described herein, the contrast material (i.e. the treated water 20) is omitted and the device 30 emits the electromagnetic radiation at the subject and/or at the LDWE and the spectral imaging software (or programming instructions) of the digital processing unit 40 generates the spectrogram and/or image and the digital processing unit 40 determines, after generating the spectrogram and/or image, a water fingerprint of the LDWE and then determines whether the subject has one or more of the various conditions and then may output the determination.

Another embodiment is a method of non-contact rapid diagnosis of a subject, the method making use of a water Object associated with the subject, without active participation of the subject, the method comprising:

A step of discharging electrochemically treated water toward a low disperse water envelope (LDWE) emitted by the subject, the LDWE surrounding the subject so as to be within 5 meters (or within 1 meter or within half a meter) of the subject, so as to form a water mixture envelope;

A further step of transmitting electromagnetic radiation having a wavelength in the UV range or visible light range, using at least one frequency-stabilized laser device, toward the subject or an area surrounding the subject containing the water mixture envelope;

An additional step of using an analog to digital converter that receives a reflected beam and generating, using a spectral imaging software (or programming instructions) of a digital processing unit, (i) a spectrogram or (ii) both a spectrogram and an image derived from the spectrogram, from the digitized reflected beam using a Fourier transform or other signal analysis algorithm;

Another step of executing instructions, by a digital processing unit, to perform:

storing reference spectra of healthy subjects and ill subjects on a non-transitory computer readable storage medium, each of the ill subjects suffering from one or more medical conditions, the variety of medical conditions comprise brain hemorrhage, brain cancer, cancer of the pancreas, diabetes, a sexually transmitted disease and diseases caused by pathogens in the subject's body and finding a first pattern of frequencies in the reference spectra of the healthy subjects and ill subjects based on one or more of an amplitude, phase shift, frequency shift and a chemical shift of frequencies in the reference spectra, wherein the reference spectra derive from one or more imaging techniques including PET CT, CT, MRI, and the frequency-stabilized laser scanning the brain or the pancreas;

deriving a first pattern of concentrations of electrolytes and protein molecules in the stored reference spectra from the first pattern of frequencies using neural networks;

determining, using the spectrogram and/or image, a second pattern of frequencies in water spectra of the subject based on one or more of an amplitude, phase shift, frequency shift and a chemical shift in the water spectra of the subject, and derive a second pattern of concentrations of electrolytes and protein molecules in the water mixture envelope of the subject from the second pattern of frequencies using the neural networks;

compare the first pattern of concentrations with the second pattern of concentrations;

determining, based on the comparing of the first and second pattern of concentrations, at least a preliminary indication of whether the subject suffers from one or more of the variety of medical conditions by executing pattern recognition software; and outputting the determination.

One method is a method of non-contact rapid diagnosis of a subject, the method making use of a water Object associated with the subject, without active participation of the subject, the method comprising:

discharging electrochemically treated water toward a low disperse water envelope (LDWE) emitted by the subject, the LDWE surrounding the subject so as to be within 5 meters of the subject, so as to form a water mixture envelope;

transmitting electromagnetic radiation having a wavelength in the UV range or visible light range, using at least one frequency-stabilized laser device, toward the subject or an area surrounding the subject containing the water mixture envelope;

using an analog to digital converter to receive a reflected beam and generating, using the analog to digital converter a digitized reflected beam;

executing instructions, by a digital processing unit, to perform:

using a signal analysis algorithm such as a Fourier transform to generate from the digitized reflected beam (i) a spectrogram or (ii) both a spectrogram and an image derived from the spectrogram, storing reference spectra of healthy subjects and ill subjects on a non-transitory computer readable storage medium, each of the ill subjects suffering from one or more medical conditions, the medical conditions comprise brain hemorrhage, brain cancer and cancer of the pancreas, (and may also include diabetes, a sexually transmitted disease and diseases caused by pathogens in the subject's body) and finding a first pattern of frequencies in the reference spectra of the healthy subjects and ill subjects based on one or more of an amplitude, phase shift, frequency shift and a chemical shift of frequencies in the reference spectra, wherein the reference spectra derive from one or more imaging techniques including PET CT, CT, MRI, and the frequency-stabilized laser scanning the brain or the pancreas;

deriving a first pattern of concentrations of electrolytes and protein molecules in the stored reference spectra from the first pattern of frequencies using neural networks;

determining, using the one or both of the spectrogram and/or image, a second pattern of frequencies in water spectra of the subject based on one or more of an amplitude, phase shift, frequency shift and a chemical shift in the water spectra of the subject, and derive a second pattern of concentrations of electrolytes and protein molecules in the water mixture envelope of the subject from the second pattern of frequencies using the neural networks;

compare the first pattern of concentrations with the second pattern of concentrations;

determining, based on the comparing of the first and second pattern of concentrations, at least a preliminary indication of whether the subject suffers from one or more of the variety of medical conditions by executing pattern recognition software; and outputting the determination.

As used herein, the term "about" may be used to specify a value of a quantity or parameter (e.g., the length of an element or a wavelength of radiation) to within a continuous range of values in the neighborhood of (and including) a given (stated) value. For example, "about" specifies the value of a parameter to be between 95% and 105% of the given value. For example, the statement "the length of the element is equal to about 1 mm" is equivalent to the statement "the length of the element is between 0.95 mm and 1.05 mm.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A non-contact rapid diagnostic system, comprising:

water that has been treated electrochemically so as to remove impurities;

at least one frequency-stabilized laser device configured to generate electromagnetic radiation of a wavelength in the UV range or in the visible light range and positionable so as to direct the electromagnetic radiation toward a human subject and toward an area external to the subject and surrounding a head, torso and/or legs of the subject, the area containing a water mixture envelope comprising (i) a mist or sprayed form of the electrochemically treated water and (ii) a low disperse water envelope (LDWE) emitted from the subject's body, the LDWE including emissions from the subject's body other than by exhalation;

at least one mist-generation device configured and positioned so as to spray the electrochemically treated water into open air surrounding the subject;

at least one optical detector configured to receive the reflected electromagnetic radiation and generate an analog signal corresponding thereto;

an analog to digital converter configured to receive the analog signal and generated a digitized reflected beam;

a processor configured to:

using a signal analysis algorithm, generate (i) a spectrogram from the digitized reflected beam or (ii) both the spectrogram and an image derived from the spectrogram, store reference spectra of healthy subjects having healthy brains and ill subjects on a non-transitory computer readable storage medium, each of the ill subjects previously determined by CT, PET CT or MRI to have one of the following three medical conditions: intracranial brain hemorrhage, brain cancer or cancer of the pancreas, and find a first pattern of frequencies in the reference spectra based on one or more of an amplitude, phase shift, frequency shift and a chemical shift of frequencies in the reference spectra, wherein the reference spectra derive from one or more imaging techniques including PET CT, CT, MRI, and the frequency-stabilized laser scanning the brain or the pancreas;

derive a first pattern of concentrations of electrolytes and protein molecules in the stored reference spectra from the first pattern of frequencies using neural networks;

determine, after generating the spectrogram or both the spectrogram and the image, a second pattern of frequencies in the spectrogram derived from the digitized reflected beam, based on one or more of an amplitude, phase shift, frequency shift and a chemical shift in the spectrogram of the subject, and derive a second pattern of concentrations of electrolytes and protein molecules in the water mixture envelope of the subject from the second pattern of frequencies using the neural networks;

compare the first pattern of concentrations with the second pattern of concentrations;

determine, based on the comparing of the first and second pattern of concentrations, at least a preliminary indication of whether the subject suffers from one of: brain hemorrhage, brain cancer and cancer of the pancreas by executing pattern recognition software including by distinguishing, for each particular medical condition of the three medical conditions, between (i) subjects having a preliminary indication of the particular medical condition and (ii) healthy subjects;

and an output unit configured to receive data and output the determination, wherein the system is configured to operate without requiring active participation by the subject.

2. The system of claim 1, wherein the second pattern of frequencies of the subject indicates a resonance density of at least seven, wherein the resonance density is a total number of resonance frequency peaks in the spectrogram.

3. The system of claim 1, wherein the processor creates an unsupervised training set from the references spectra of the healthy and ill subjects.

4. The system of claim 1, wherein the treated water is configured to act as a contrast material vis a vis the LDWE so as to increase a signal to noise ratio and thereby facilitate processing of the one or both of the spectrogram and the image of the reflected beam reflected from the laser device.

5. The system of claim 4, wherein the reflected beam has an electromagnetic frequency of the reflected laser.

6. The system of claim 1, wherein the water mixture envelope comprises particles of 1-60 microns in diameter.

7. The system of claim 1, wherein the electromagnetic radiation comprises a laser beam having a range of wavelengths from 600 nm to 685 nm and wherein the laser device is configured to direct the laser beam.

8. The system of claim 1, further comprising an infra red emitter configured to emit electromagnetic radiation having a wavelength from 1050 nm to 2900 nm.

9. The system of claim 1, further comprising an infra red emitter and wherein the processor is configured to obtain (i) an external water fingerprint from a spectroscopic analysis of the one or both of the spectrogram and image from the reflected beam that was reflected from the electromagnetic radiation emitted by the laser device and (ii) a general water fingerprint of both the water mixture envelope external to the subject and of water internal to the body of the subject derived from signal from the reflected beam that was reflected from the electromagnetic radiation emitted by the infra red emitter, and to compare each of the external and general water spectra with the stored spectra.

10. The system of claim 1, further comprising a terahertz device wherein the electromagnetic radiation that is emitted by the terahertz device has a frequency of 1.0·10ˆ5 MHz to 1.0·10ˆ7 MHz.

11. The system of claim 1, wherein the electromagnetic radiation emitted by the at least one laser device is non-ionizing UV radiation that has a wavelength of 320 nm to 385 nm.

12. The system of claim 1, wherein the processor is configured to perform a spectral analysis of an external water spectra and of a general water spectra to distinguish between healthy and ill subjects based on a magnitude of a resonance density, wherein the resonance density is a total number of resonance frequency peaks in the spectrogram.

13. The system of claim 1, further comprising mirrors configured to mechanically adjust a beam of the laser device via an alignment of the mirrors, the laser device configured to be adjusted electrically by adjusting one or more of a frequency and a power of the laser device so as to select a depth of penetration of a laser beam into the water mixture envelope in order to scan different layers of the water mixture envelope.

14. The system of claim 1, further comprising an infra red emitter positioned 2 to 5 meters from the subject.

15. The system of claim 1, wherein the at least one frequency-stabilized laser device is a helium-neon laser device.

16. The system of claim 1, wherein a fractional frequency stability of the frequency-stabilized laser device is <7×10ˆ−16.

17. The system of claim 1, wherein the water that has been treated electrochemically is water that has been treated by electrocoagulation and has been prepared by an electrochemical process that utilized an oxidative reduction potential (ORP) of between −800 mV and −400 mV.

18. The system of claim 1, wherein the water that has been treated electrochemically is water that has been treated by electrocoagulation and has been prepared by an electrochemical process that utilized an oxidative reduction potential (ORP) of between −800 mV and −400 mV.

19. A method of non-contact rapid diagnosis of a human subject, the method making use of a water Object associated with the subject, without active participation of the subject, the method comprising:

discharging electrochemically treated water from which impurities have been removed using at least one mist-generation device configured to spray the electrochemically treated water into open air surrounding the subject toward a low disperse water envelope (LDWE) emitted by the subject and external to the subject, the LDWE surrounding the subject so as to be within 5 meters of the subject, so as to form a water mixture envelope, the LDWE including emissions from the subject's body other than by exhalation;

transmitting electromagnetic radiation having a wavelength in the UV range or visible light range, using at least one frequency-stabilized laser device, toward the subject and toward an area external to the subject and surrounding a head, torso and/or legs of the subject containing the water mixture envelope, the portions ranging from a head of the subject to the legs of the subject;

using at least one optical detector to receive the reflected electromagnetic radiation and generate an analog signal corresponding thereto;

using an analog to digital converter to receive the analog signal and generate a digitized reflected beam;

executing instructions, by a processor, to perform:

using a signal analysis algorithm, generating from the digitized reflected beam (i) a spectrogram or (ii) the spectrogram and an image derived from the spectrogram;

storing reference spectra of healthy subjects and ill subjects on a non-transitory computer readable storage medium, each of the ill subjects suffering from one of the following three medical conditions: brain hemorrhage, brain cancer and cancer of the pancreas, and finding a first pattern of frequencies in the reference spectra of the healthy subjects and ill subjects based on one or more of an amplitude, phase shift, frequency shift and a chemical shift of frequencies in the reference spectra, wherein the reference spectra derive from one or more imaging techniques including PET CT, CT, MRI, and the frequency-stabilized laser scanning the brain or the pancreas;

deriving a first pattern of concentrations of electrolytes and protein molecules in the stored reference spectra from the first pattern of frequencies using neural networks;

determining, using (i) the spectrogram or (ii) the spectrogram and the image, a second pattern of frequencies in spectrogram derived from the digitized reflected beam based on one or more of an amplitude, phase shift, frequency shift and a chemical shift in the spectrogram of the subject, and derive a second pattern of concentrations of electrolytes and protein molecules in the water mixture envelope of the subject from the second pattern of frequencies using the neural networks;

compare the first pattern of concentrations with the second pattern of concentrations;

determining, based on the comparing of the first and second pattern of concentrations, at least a preliminary indication of whether the subject suffers from any of: brain hemorrhage, brain cancer and cancer of the pancreas by executing pattern recognition software including by distinguishing, for each particular medical condition of the three medical conditions, between (i) subjects having a preliminary indication of the particular medical condition and (ii) healthy subjects; and outputting the determination.

20. A non-contact rapid diagnostic system, comprising:

water that has been treated electrochemically so as to remove impurities;

at least one frequency-stabilized laser device configured to generate electromagnetic radiation of a wavelength in the UV range or in the visible light range and positionable so as to direct the electromagnetic radiation toward a human subject and toward an area external to the subject and surrounding a head, torso and/or legs of the subject, the area containing a water mixture envelope comprising (i) a mist or sprayed form of the electrochemically treated water and (ii) a low disperse water envelope (LDWE) emitted from the subject's body, the LDWE including emissions from the subject's body other than by exhalation;

at least one mist-generation device configured and positioned so as to spray the electrochemically treated water into open air surrounding the subject;

at least one optical detector configured to receive the reflected electromagnetic radiation and generate an analog signal corresponding thereto;

an analog to digital converter configured to receive the analog signal and generated a digitized reflected beam;

a processor configured to:

using a signal analysis algorithm, generate (i) a spectrogram from the digitized reflected beam or (ii) both the spectrogram and an image derived from the spectrogram, store reference spectra of healthy subjects having healthy brains and ill subjects on a non-transitory computer readable storage medium, each of the ill subjects previously determined by CT, PET CT or MRI to have an intracranial brain hemorrhage in a hemisphere of the brain, and find a first pattern of frequencies in the reference spectra based on one or more of an amplitude, phase shift, frequency shift and a chemical shift of frequencies in the reference spectra, wherein the reference spectra derive from one or more imaging techniques including PET CT, CT, MRI, and the frequency-stabilized laser scanning the brain;

derive a first pattern of concentrations of electrolytes and protein molecules in the stored reference spectra from the first pattern of frequencies using neural networks;

determine, after generating the spectrogram or both the spectrogram and the image, a second pattern of frequencies in the spectrogram derived from the digitized reflected beam, based on one or more of an amplitude, phase shift, frequency shift and a chemical shift in the spectrogram of the subject, and derive a second pattern of concentrations of electrolytes and protein molecules in the water mixture envelope of the subject from the second pattern of frequencies using the neural networks;

compare the first pattern of concentrations with the second pattern of concentrations;

determine, based on the comparing of the first and second pattern of concentrations, at least a preliminary indication of whether the subject suffers from brain hemorrhage by executing pattern recognition software including by distinguishing between (i) subjects having a preliminary indication of a brain hemorrhage and (ii) healthy subjects;

and an output unit configured to receive data and output the determination, wherein the system is configured to operate without requiring active participation by the subject.

21. The system of claim 20, wherein the electromagnetic radiation comprises a laser beam having a range of wavelengths from 600 nm to 685 nm and wherein the laser device is configured to direct the laser beam.

22. The system of claim 20, further comprising an infra red emitter configured to emit electromagnetic radiation having a wavelength from 1050 nm to 2900 nm.

23. The system of claim 20, further comprising a terahertz device wherein the electromagnetic radiation that is emitted by the terahertz device has a frequency of 1.0·10^5 MHz to 1.0·10^7 MHz.

24. The system of claim 20, wherein the electromagnetic radiation emitted by the at least one laser device is non-ionizing UV radiation that has a wavelength of 320 nm to 385 nm.

25. The system of claim 20, wherein the processor is configured to perform a spectral analysis of an external water spectra and of a general water spectra to distinguish between healthy and ill subjects based on a magnitude of a resonance density, wherein the resonance density is a total number of resonance frequency peaks in the spectrogram.

26. The system of claim 20, further comprising mirrors configured to mechanically adjust a beam of the laser device via an alignment of the mirrors, the laser device configured to be adjusted electrically by adjusting one or more of a frequency and a power of the laser device so as to select a depth of penetration of a laser beam into the water mixture envelope in order to scan different layers of the water mixture envelope.

27. The system of claim 20, wherein the at least one frequency-stabilized laser device is a helium-neon laser device.

28. The system of claim 20, wherein a fractional frequency stability of the frequency-stabilized laser device is <1.5×10^−15.

* * * * *